(12) United States Patent
Chen et al.

(10) Patent No.: US 8,252,303 B2
(45) Date of Patent: *Aug. 28, 2012

(54) INJECTABLE DEPOT COMPOSITIONS AND USES THEREOF

(75) Inventors: Guohua Chen, Sunnyvale, CA (US); Paul R. Houston, Hayward, CA (US); Lothar Walter Kleiner, Los Altos, CA (US); John J. Spaltro, Asbury, NJ (US)

(73) Assignee: Durect Corporation, Cupertino, CA (US)

( * ) Notice: Subject to any disclaimer, the term of this patent is extended or adjusted under 35 U.S.C. 154(b) by 928 days.

This patent is subject to a terminal disclaimer.

(21) Appl. No.: 10/295,814

(22) Filed: Nov. 14, 2002

(65) Prior Publication Data

US 2004/0024069 A1 Feb. 5, 2004

Related U.S. Application Data

(60) Provisional application No. 60/399,882, filed on Jul. 31, 2002.

(51) Int. Cl.
*A61F 2/00* (2006.01)
*A61K 47/30* (2006.01)

(52) U.S. Cl. ................. 424/426; 424/423; 514/772.3

(58) Field of Classification Search ............. 424/426, 424/489, 423; 514/772.3
See application file for complete search history.

(56) References Cited

U.S. PATENT DOCUMENTS

| | | | |
|---|---|---|---|
| 3,797,492 A | 3/1974 | Place | 128/260 |
| 3,923,939 A | 12/1975 | Baker et al. | 264/49 |
| 3,987,790 A | 10/1976 | Eckenhoff et al. | 128/260 |
| 4,008,719 A | 2/1977 | Theeuwes et al. | 128/260 |
| 4,443,340 A | 4/1984 | May et al. | 210/697 |
| 4,568,559 A | 2/1986 | Nuwayser et al. | 427/3 |
| 4,623,588 A | 11/1986 | Nuwayser et al. | 428/402.24 |
| 4,668,506 A | 5/1987 | Bawa | 424/429 |
| 4,708,861 A | 11/1987 | Popescu et al. | 424/1.1 |
| 4,711,782 A | 12/1987 | Okada et al. | 424/455 |
| 4,713,244 A | 12/1987 | Bawa et al. | 424/429 |
| 4,853,218 A | 8/1989 | Yim et al. | 424/85.7 |
| 4,865,845 A | 9/1989 | Eckenhoff et al. | 424/424 |
| 4,866,050 A | 9/1989 | Ben-Amoz | 514/179 |
| 4,931,279 A | 6/1990 | Bawa et al. | 424/427 |
| 4,938,763 A | 7/1990 | Dunn et al. | 604/891.1 |
| 4,985,404 A | 1/1991 | Mitchell et al. | 514/6 |

(Continued)

FOREIGN PATENT DOCUMENTS

WO WO 93/24150 12/1993

(Continued)

OTHER PUBLICATIONS

Cleland, J. L. "Injectable Gels for Local and Systemic Delivery of Proteins," *Proceed. Int'l. Symp. Contr I. Rel. Bioact. Mater.*, vol. 28, 2001.

(Continued)

*Primary Examiner* — Blessing Fubara

(57) ABSTRACT

Injectable depot compositions are provided that include a bioerodible, biocompatible polymer, a solvent having a miscibility in water of less than or equal to 7 wt. % at 25° C., in an amount effective to plasticize the polymer and form a gel therewith, a thixotropic agent, and a beneficial agent. The solvent comprises an aromatic alcohol, an ester of an aromatic acid, an aromatic ketone, or mixtures thereof. The compositions have substantially improved the shear thinning behavior and reduced injection force, rendering the compositions readily implanted beneath a patient's body surface by injection.

44 Claims, 21 Drawing Sheets

U.S. PATENT DOCUMENTS

| | | | |
|---|---|---|---|
| 5,019,400 A | 5/1991 | Gombotz et al. | 424/497 |
| 5,057,318 A | 10/1991 | Magruder et al. | 424/438 |
| 5,059,423 A | 10/1991 | Magruder et al. | 424/438 |
| 5,061,492 A | 10/1991 | Okada et al. | 424/423 |
| 5,077,033 A | 12/1991 | Viegas et al. | 514/668 |
| 5,085,866 A | 2/1992 | Cowsar et al. | 424/481 |
| 5,112,614 A | 5/1992 | Magruder et al. | 424/422 |
| 5,137,727 A | 8/1992 | Eckenhoff | 424/422 |
| 5,151,093 A | 9/1992 | Theeuwes et al. | 604/892.1 |
| 5,181,914 A | 1/1993 | Zook | 604/307 |
| 5,209,746 A | 5/1993 | Balaban et al. | 604/892.1 |
| 5,234,692 A | 8/1993 | Magruder et al. | 424/473 |
| 5,234,693 A | 8/1993 | Magruder et al. | 424/473 |
| 5,242,910 A | 9/1993 | Damanj | 514/152 |
| 5,252,318 A | 10/1993 | Joshi et al. | 424/78.04 |
| 5,278,201 A | 1/1994 | Dunn et al. | 523/133 |
| 5,279,608 A | 1/1994 | Cheikh | 604/892.1 |
| 5,300,295 A | 4/1994 | Viegas et al. | 424/427 |
| 5,308,348 A | 5/1994 | Balaban et al. | 644/891.1 |
| 5,310,865 A | 5/1994 | Enomoto et al. | 528/361 |
| 5,324,519 A | 6/1994 | Dunn et al. | 424/426 |
| 5,330,452 A | 7/1994 | Zook | 604/307 |
| 5,336,057 A | 8/1994 | Fukuda et al. | 417/395 |
| 5,340,614 A | 8/1994 | Perman et al. | 427/2.24 |
| 5,342,627 A | 8/1994 | Chopra et al. | 424/473 |
| 5,415,866 A | 5/1995 | Zook | 424/448 |
| 5,441,732 A | 8/1995 | Hoeg et al. | 424/78.04 |
| 5,447,725 A | 9/1995 | Damani et al. | 424/435 |
| 5,456,679 A | 10/1995 | Balaban et al. | 604/892.1 |
| 5,487,897 A | 1/1996 | Polson et al. | 424/426 |
| 5,540,912 A | 7/1996 | Roorda et al. | 424/422 |
| 5,543,156 A | 8/1996 | Roorda et al. | 424/484 |
| 5,556,905 A | 9/1996 | Frappier et al. | 524/311 |
| 5,571,525 A | 11/1996 | Roorda et al. | 424/426 |
| 5,587,175 A | 12/1996 | Viegas et al. | 424/427 |
| 5,599,534 A | 2/1997 | Himmelstein et al. | 424/78.04 |
| 5,599,552 A | 2/1997 | Dunn et al. | 424/423 |
| 5,610,184 A | 3/1997 | Shahinian, Jr. | 514/540 |
| 5,618,563 A | 4/1997 | Berde et al. | 424/501 |
| 5,620,700 A | 4/1997 | Berggren et al. | 424/435 |
| 5,651,986 A | 7/1997 | Brem et al. | 424/484 |
| 5,654,010 A | 8/1997 | Johnson et al. | 424/502 |
| 5,656,297 A | 8/1997 | Bernstein et al. | 424/484 |
| 5,660,817 A | 8/1997 | Masterman et al. | 424/49 |
| 5,674,292 A | 10/1997 | Tucker et al. | 623/16 |
| 5,681,873 A | 10/1997 | Norton et al. | 523/115 |
| 5,700,485 A | 12/1997 | Berde et al. | 424/501 |
| 5,707,644 A | 1/1998 | Illum | 424/434 |
| 5,708,011 A | 1/1998 | Bardsley et al. | 514/330 |
| 5,733,950 A | 3/1998 | Dunn et al. | 523/113 |
| 5,744,153 A | 4/1998 | Yewey et al. | 424/426 |
| 5,747,058 A | 5/1998 | Tipton et al. | 424/337 |
| 5,747,060 A | 5/1998 | Sackler et al. | 424/426 |
| 5,759,563 A | 6/1998 | Yewey et al. | 424/426 |
| 5,760,077 A | 6/1998 | Shahinian, Jr. | 514/540 |
| 5,766,637 A | 6/1998 | Shine et al. | 424/497 |
| 5,780,044 A | 7/1998 | Yewey et al. | 424/426 |
| 5,783,205 A | 7/1998 | Berggren et al. | 424/426 |
| 5,804,212 A | 9/1998 | Illum | 424/434 |
| 5,849,763 A | 12/1998 | Bardsley et al. | 514/445 |
| 5,910,502 A | 6/1999 | Gennery | 514/330 |
| 5,919,835 A | 7/1999 | Domb et al. | 523/113 |
| 5,922,340 A | 7/1999 | Berde et al. | 424/426 |
| 5,942,241 A | 8/1999 | Chasin et al. | 424/426 |
| 5,955,479 A | 9/1999 | Bardsley et al. | 514/330 |
| 5,958,443 A | 9/1999 | Viegas et al. | 424/427 |
| 5,972,326 A | 10/1999 | Galin et al. | 424/78.04 |
| 5,972,366 A | 10/1999 | Haynes et al. | 424/422 |
| 5,990,194 A | 11/1999 | Dunn et al. | 523/113 |
| 6,004,295 A | 12/1999 | Langer et al. | 604/164 |
| 6,046,187 A | 4/2000 | Berde et al. | 514/180 |
| 6,050,986 A | 4/2000 | Hektner | 604/508 |
| 6,086,909 A | 7/2000 | Harrison et al. | 424/430 |
| 6,103,266 A | 8/2000 | Tapolski et al. | 424/484 |
| 6,106,301 A | 8/2000 | Merril | 434/262 |
| 6,117,425 A | 9/2000 | MacPhee et al. | 424/94.64 |
| 6,120,789 A | 9/2000 | Dunn | 424/426 |
| 6,120,804 A | 9/2000 | Drizen et al. | 424/488 |
| 6,129,933 A | 10/2000 | Oshlack et al. | 424/495 |
| 6,130,200 A * | 10/2000 | Brodbeck et al. | 514/2 |
| 6,136,334 A | 10/2000 | Viegas et al. | 424/427 |
| 6,143,314 A | 11/2000 | Chandrashekar et al. | 424/426 |
| 6,193,991 B1 | 2/2001 | Shukla | 424/426 |
| 6,193,994 B1 | 2/2001 | Lee et al. | 424/444 |
| 6,197,327 B1 | 3/2001 | Harrison et al. | 424/430 |
| 6,214,387 B1 | 4/2001 | Berde et al. | 424/501 |
| 6,217,911 B1 | 4/2001 | Vaung et al. | 424/501 |
| 6,238,702 B1 | 5/2001 | Berde et al. | 424/489 |
| 6,248,345 B1 | 6/2001 | Goldenheim et al. | 424/426 |
| 6,255,502 B1 | 7/2001 | Penkler et al. | 552/549 |
| 6,261,547 B1 | 7/2001 | Bawa et al. | 424/78.04 |
| 6,309,375 B1 | 10/2001 | Glines et al. | 604/187 |
| 6,322,548 B1 | 11/2001 | Payne et al. | 604/500 |
| 6,331,311 B1 * | 12/2001 | Brodbeck et al. | 424/425 |
| 6,352,667 B1 | 3/2002 | English | 264/328.17 |
| 6,355,273 B1 | 3/2002 | Carli et al. | 424/489 |
| 6,372,245 B1 | 4/2002 | Bowman et al. | 424/427 |
| 6,375,659 B1 | 4/2002 | Erbe et al. | 606/94 |
| 6,395,293 B2 | 5/2002 | Polson et al. | 424/426 |
| 6,403,057 B1 | 6/2002 | Schneider et al. | 424/9.52 |
| 6,417,201 B1 | 7/2002 | Bardsley et al. | 514/330 |
| 6,423,818 B1 | 7/2002 | Matsuda et al. | 528/354 |
| 6,426,339 B1 | 7/2002 | Berde et al. | 514/180 |
| 6,432,415 B1 | 8/2002 | Osborne et al. | 424/400 |
| 6,451,346 B1 | 9/2002 | Shah | 424/486 |
| 6,534,081 B2 | 3/2003 | Goldenheim et al. | 424/426 |
| 2001/0004644 A1 | 6/2001 | Levin | 514/646 |
| 2001/0037104 A1 | 11/2001 | Zhang et al. | 604/502 |
| 2001/0046518 A1 | 11/2001 | Sawhney | 424/486 |
| 2001/0055607 A1 | 12/2001 | Levin | 424/435 |
| 2002/0001608 A1 | 1/2002 | Polson et al. | 424/426 |
| 2002/0004063 A1 | 1/2002 | Zhang | 424/443 |
| 2002/0010150 A1 | 1/2002 | Cortese et al. | 514/54 |
| 2002/0015712 A1 | 2/2002 | Mchride et al. | 424/400 |
| 2002/0016338 A1 | 2/2002 | Mather et al. | 514/317 |
| 2002/0028181 A1 | 3/2002 | Miller et al. | 424/43 |
| 2002/0028243 A1 | 3/2002 | Masters | 424/484 |
| 2002/0037358 A1 | 3/2002 | Barry et al. | 427/2.1 |
| 2002/0039594 A1 | 4/2002 | Unger | 424/426 |
| 2002/0045668 A1 | 4/2002 | Dang et al. | 514/649 |
| 2002/0054915 A1 | 5/2002 | Goldenheim et al. | 424/497 |
| 2002/0061326 A1 | 5/2002 | Li et al. | 424/424 |
| 2002/0086971 A1 | 7/2002 | Pham | 528/354 |

FOREIGN PATENT DOCUMENTS

| | | |
|---|---|---|
| WO | WO 95/13799 | 5/1995 |
| WO | WO 98/27962 | 7/1998 |
| WO | WO 98/27963 | 7/1998 |
| WO | WO 99/47073 | 9/1999 |
| WO | WO 00/74650 A2 | 12/2000 |
| WO | WO 02/058670 A1 | 8/2002 |
| WO | WO 02/067991 A1 | 9/2002 |
| WO | WO 03/041684 A2 | 5/2003 |
| WO | WO 03/041685 A1 | 5/2003 |
| WO | WO 03/041757 A2 | 5/2003 |

OTHER PUBLICATIONS

Blanco, M. D. et al. "Bupivacaine-loaded comatrix formed by alumin microspheres included in a poly(lactide-coglycolide) film: in vivo biocompatibility and drug release studies," *Biomaterials*, vol. 20, pp. 1919-1924, 1999.

Duenas, E. et al. "Sustained Delivery of rhVEGF from a Novel Injectable Liquid, Plad" *Proceed. Int'l. Symp. Control. Rel. Bioact. Mater.*, vol. 28, 2001.

Guevello, P. Le at al. "High-performance liquid chromatographic determination of bupivacaine in plasma samples for biopharmaveutical studies and application to seven other local anaesthetics," *Journal of Chromatography*, vol. 622, pp. 284-290, (1993).

Garry, M. G. et al. "Evaluation of the efficency of a bioerodible bupivacaine polymer system n antinociception and inflammatory mediator release," *Pain*, vol. 82, pp. 49-55, 1999.

Lambert, W. J. at al. "Development of an in situ forming bidegradable poly-lactide-co-glycolide system for controlled release of proteins," *Journal of Controlled Release*, vol. 33, pp. 189-195 (1995).

Okumu, F. W. et al. "Sustained Delivery of Growth Hormone from a Novel Injectable Liquid, Plad," *Proceed. Int'l. Symp. Control. Rel. Bioact. Mater.*, vol. 28, 2001.

Okumu, F. W. et al. "Evaluation of the Saber™ Delivery System for Sustained Release of Growth Hormone—Formulation Design and In Vivo Assessment," *Proceed. Int'l. Symp. Control. Rel. Bioact. Mater.*, vol. 28, 2001.

Philip, B. K. et al. "The Economoc Impact of Opiods on Postoperative Pain Management," *Journal of Clinical Anesthesia*, vol. 14, pp. 354-364, 2002.

* cited by examiner

INJECTABLE DEPOT COMPOSITIONS AND USES THEREOF

CROSS-REFERENCE TO RELATED APPLICATION

This application claims the benefit of U.S. Provisional Application No. 60/399,882 filed on Jul. 31, 2002.

BACKGROUND OF THE INVENTION

1. Field of the Invention

The present invention relates to a depot composition that can be injected into a desired location within a patient's body to form an implant, which provides for sustained release of a beneficial agent. More particularly, the present invention pertains to depot compositions that exhibit improved shear thinning behavior and a low injection force. The present invention also relates to a method of using the depot composition to administer a beneficial agent to a patient.

2. Description of the Related Art

Biodegradable polymers have been used for many years in medical applications. Illustrative devices composed of the biodegradable polymers include sutures, surgical clips, staples, implants, and drug delivery systems. The majority of these biodegradable polymers have been based upon glycolide, lactide, caprolactone, and copolymers thereof.

The biodegradable polymers can be thermoplastic materials, meaning that they can be heated and formed into various shapes such as fibers, clips, staples, pins, films, etc. Alternatively, they can be thermosetting materials formed by cross-linking reactions, which lead to high molecular-weight materials that do not melt or form flowable liquids at high temperatures. Although thermoplastic and thermosetting biodegradable polymers have many useful biomedical applications, there are several important limitations to their use in the bodies of various animals including humans, animals, birds, fish, and reptiles.

Solid implant drug delivery systems containing a drug incorporated in thermoplastic or thermosetting biodegradable polymers have been widely used successfully. Such implants have to be inserted into the body through an incision which is sometimes larger than desired by the medical profession and occasionally lead to a reluctance of the patients to accept such an implant or drug delivery system. The following U.S. Pat. Nos. 5,456,679; 5,336,057; 5,308,348; 5,279,608; 5,234,693; 5,234,692; 5,209,746; 5,151,093; 5,137,727; 5,112,614; 5,085,866; 5,059,423; 5,057,318; 4,865,845; 4,008,719; 3,987,790 and 3,797,492 are believed to be representative of such drug delivery systems and are incorporated herein by reference. These patents disclose reservoir devices, osmotic delivery devices and pulsatile delivery devices for delivering beneficial agents.

Injecting drug delivery systems as small particles, microspheres, or microcapsules avoids the incision needed to implant drug delivery systems. However, these materials do not always satisfy the demand for a biodegradable implant. These materials are particulate in nature, do not form a continuous film or solid implant with the structural integrity needed for certain prostheses, the particles tend to aggregate and thus their behavior is hard to predict. When inserted into certain body cavities such as a mouth, a periodontal pocket, the eye, or the vagina, where there is considerable fluid flow, these small particles, microspheres, or microcapsules are poorly retained because of their small size and discontinuous nature. Further, if there are complications, removal of microcapsule or small-particle systems from the body without extensive surgical intervention is considerably more difficult than with solid implants. Additionally, manufacture, storage and injectability of microspheres or microcapsules prepared from these polymers and containing drugs for release into the body present problems.

The art has developed various drug delivery systems in response to the aforementioned challenges. The following U.S. Pat. Nos. 5,990,194; 5,780,044; 5,733,950; 5,620,700; 5,599,552; 5,556,905 5,278,201; 5,242,910 and 4,938,763; and PCT publication WO98/27962 are believed to be representative and are incorporated herein by reference. These patents disclose polymer compositions for injectable implants using solvents and/or plasticizers.

Previously described polymer compositions for injectable implants have used solvent/plasticizers that are very or relatively soluble in aqueous body fluids to promote rapid solidification of the polymer at the implant site and promote diffusion of drug from the implant. Rapid migration of water into such polymeric implants utilizing water soluble polymer solvents, when the implants are placed in the body and exposed to aqueous body fluids, presents a serious problem. The rapid water uptake often results in implants having pore structures that are nonhomogeneous in size and shape. Typically, the surface pores take on a finger-like pore structure extending for as much as one-third of a millimeter or more from the implant surface into the implant, and such finger-like pores are open at the surface of the implant to the environment of use. The internal pores tend to be smaller and less accessible to the fluids present in the environment of use. The rapid water uptake characteristic often results in uncontrolled release of beneficial agent that is manifested by an initial, rapid release of beneficial agent from the polymer composition, corresponding to a "burst" of beneficial agent being released from the implant. The burst often results in a substantial portion of the beneficial agent, if not all, being released in a very short time, e.g., hours or 1-2 days. Such an effect can be unacceptable, particularly in those circumstances where a controlled delivery is desired, i.e., delivery of beneficial agent in a controlled manner over a period of greater than two weeks or up to a month, or where there is a narrow therapeutic window and release of excess beneficial agent can result in adverse consequences to the subject being treated, or where it is necessary to mimic the naturally-occurring daily profile of beneficial agents, such as hormones and the like, in the body of the subject being treated.

Accordingly, when such devices are implanted, the finger-like pores allow very rapid uptake of aqueous body fluids into the interior of the implant with consequent immediate and rapid dissolution of significant quantities of beneficial agent and unimpeded diffusion of beneficial agent into the environment of use, producing the burst effect discussed above.

Furthermore, rapid water uptake can result in premature polymer precipitation such that a hardened implant or one with a hardened skin is produced. The inner pores and much of the interior of the polymer containing beneficial agent are shut off from contact with the body fluids and a significant reduction in the release of beneficial agent can result over a not insignificant period of time ("lag time"). That lag time is undesirable from the standpoint of presenting a controlled, sustained release of beneficial agent to the subject being treated. What one observes, then, is a burst of beneficial agent being released in a short time period immediately after implantation, a lag time in which no or very little beneficial agent is being released, and subsequently continued delivery of beneficial agent (assuming beneficial agent remains after the burst) until the supply of beneficial agent is exhausted.

Various approaches to control burst and modulate and stabilize the delivery of the beneficial agent have been described. The following U.S. Pat. Nos. 6,130,200; 5,990,194; 5,780,044; 5,733,950; 5,656,297; 5,654,010; 4,985,404 and 4,853,218 and PCT publication WO 98/27962 are believed to be representative and are incorporated herein by reference. Notwithstanding some success, those methods have not been entirely satisfactory for the large number of beneficial agents that would be effectively delivered by implants.

An additional problem encountered with prior solvent-based depot compositions is that the viscosity of the injectable composition is relatively high, particularly when higher molecular weight polymers are used, and the injection force needed to introduce the composition into a patient's body is therefore high as well (see, e.g., U.S. Pat. No. 6,130,200). However, the high viscosity of the gel is desirable to maintain the integrity of the depot after injection and during the dispensing period and also to facilitate desired suspension characteristics of the beneficial agent in the gel.

To address this problem, those working in the field have employed various methods to reduce overall viscosity of the composition, such as the use of lower molecular weight polymers, a lower polymer to solvent ratio, and agents that provide viscosity reduction. See, for example, U.S. Pat. Nos. 5,733,950, 5,780,044, and 5,990,194 to Dunn et al., and International application WO 98/27962. These patents and publications describe the formation of a thixotropic gel composition that provides for shear thinning and more acceptable injectability of the gel, such that lower injection forces are needed to expel the gel from a syringe and also lower the likelihood of substantial discomfort to a subject by use of smaller needles than would otherwise be required.

Notwithstanding some success, the previously described systems have not been entirely satisfactory. For example, these approaches can result in drug particle settling; a higher initial release burst; relatively large amounts of emulsifying agent, e.g., about one-third of the total weight of the composition; manufacturing problems related to solvent volatility; denaturation of proteins and peptide drugs, and the like. Additionally, the requirement that the bioerodible polymer have a low molecular weight is quite restrictive from a manufacturing standpoint.

It has been discovered that in certain systems, biodegradable polymers dissolved in a suitable a polymer solvent and mixed with a thixotropic agent, result in depot compositions exhibiting substantially significantly improved shear thinning and further reduced injection force as compared to previously described depot gel formulations. These depot compositions have modified flow characteristics without the formation of an emulsion but still result in thixotropic compositions that are readily injectable through needles having a gauge that, when used, is not unduly uncomfortable to a subject. Also, use of such smaller amounts of an agent that imparts thixotropic properties to the gel may allow for smaller depot volume and mass without diminishing delivery of a required amount of beneficial agent over a prolonged period of time for an intended therapeutic effect.

SUMMARY OF THE INVENTION

The present invention is directed to the aforementioned needs in the art, and provides an injectable depot composition that exhibits improved shear thinning behavior and thereby enables further reduced injection force and use of a small diameter (e.g., 16 gauge and higher) needle. In particular, the injectable depot composition increases the shear thinning behavior and composition homogeneity, without resulting in settling of the beneficial agent. Additionally, the injectable depot composition reduces the injection force while maintaining high viscosity of the composition at low shear, thus maintaining the intactness of the composition. The composition provides sustained release of a beneficial agent while limiting any initial burst effect, and offers increased formulation flexibility with regard to the polymer/solvent ratio and the molecular weight of the bioerodible polymer.

In one aspect, then, the invention is directed to an injectable depot composition comprising:

(a) a bioerodible, biocompatible polymer (e.g., lactic acid-based polymer);

(b) a solvent having a miscibility in water of less than or equal to 7% at 25° C., in an amount effective to plasticize the polymer and form a gel therewith, wherein the solvent is an aromatic alcohol;

(c) a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and (d) a beneficial agent.

In another aspect, the invention is directed to an injectable depot composition comprising:

(a) a bioerodible, biocompatible polymer, preferably a lactic acid-based polymer;

(b) an aromatic alcohol having a miscibility in water of less than or equal to 7% at 25° C., in an amount effective to plasticize the polymer and form a gel therewith, wherein the aromatic alcohol has the structural formula (I)

$$Ar\text{-}(L)_n\text{-}OH \qquad (I)$$

in which Ar is a substituted or unsubstituted aryl or heteroaryl group, n is zero or 1, and L is a linking moiety;

(c) a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and (d) a beneficial agent.

In another aspect, the invention is directed to an injectable depot composition comprising:

(a) approximately 5 wt. % to approximately 90 wt. % of a biodegradable, biocompatible lactic acid-based polymer having an average molecular weight in the range of approximately 1,000 to approximately 120,000, preferably approximately 5,000 to approximately 50,000, more preferably approximately 8,000 to approximately 30,000;

(b) an aromatic alcohol having a miscibility in water of less than or equal to 7% at 25° C., in an amount effective to plasticize the polymer and form a gel therewith, wherein the aromatic alcohol has the structural formula (I)

$$Ar\text{-}(L)_n\text{-}OH \qquad (I)$$

in which Ar is a substituted or unsubstituted aryl or heteroaryl group, n is zero or 1, and L is a linking moiety;

(c) a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and (d) a beneficial agent.

In another aspect, the invention is directed to an injectable depot composition comprising:

(a) a bioerodible, biocompatible polymer, preferably a lactic acid-based polymer;

(b) a solvent selected from the group consisting of aromatic alcohols, esters of aromatic acids, aromatic ketones, and mixtures thereof; the solvent having a miscibility in water of less than or equal to 7% at 25° C., and present in an amount effective to plasticize the polymer and form a gel therewith;

(c) a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and (d) a beneficial agent.

In another aspect, the invention is directed to an injectable depot composition comprising:

(a) approximately 5 wt. % to approximately 90 wt. % of a biodegradable, biocompatible lactic acid-based polymer having an average molecular weight in the range of approximately 1,000 to approximately 120,000, preferably approximately 5,000 to approximately 50,000, more preferably approximately 8,000 to approximately 30,000;

(b) a solvent selected from the group consisting of an aromatic alcohol, an ester of an aromatic acid, and mixtures thereof, the solvent having a miscibility in water of less than or equal to 7% at 25° C., and present in an amount effective to plasticize the polymer and form a gel therewith, wherein the aromatic alcohol has the structural formula (I) wherein Ar, n and L are as defined above;

(c) a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and (d) a beneficial agent.

The lower alkanols are straight or branched chain alcohols having 2-6 carbon atoms as exemplified by ethanol, propanol, isopropanol and the like. A preferred thixotropic agent is ethanol. The composition may include an amount of ethanol that is greater than or equal to 0.01 weight percent and less than or equal to 15 weight percent of the combined weight of the solvent and the thixotropic agent. The composition may include an amount of ethanol that is greater than or equal to 0.1 weight percent and less than or equal to 5 weight percent of the combined weight of the solvent and the thixotropic agent. The composition may include an amount of ethanol that is greater than or equal to 0.5 weight percent and less than or equal to 5 weight percent of the combined weight of the solvent and the thixotropic agent.

In another aspect, the invention comprises a method of administering, locally or systemically, a beneficial agent to a subject which comprises implanting beneath the subject's body surface an injectable composition as described above. Preferably, the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of 12 or less, preferably 8 or less.

In another aspect, the invention pertains to an injectable depot composition and a method of administering such composition as described above, wherein the viscous gel further comprises a polymer selected from the group consisting of polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, terpolymers and mixtures thereof. In preferred embodiments, the polymer is a lactic acid-based polymer. Preferably, the lactic acid-based polymer may have an average molecular weight in the range of about 1,000 to about 120,000; preferably about 5,000 to about 50,000; and more preferably about 8,000 to about 30,000.

In preferred embodiments, the solvent is selected from the aromatic alcohol, lower alkyl and aralkyl esters of aryl acids; aryl, aralkyl and lower alkyl ketones; and lower alkyl esters of citric acid. Preferably, the solvent is selected from benzyl alcohol, benzyl benzoate and ethyl benzoate. In preferred embodiments, the composition is free of solvents having a miscibility in water that is greater than 7 wt. % at 25° C. Preferably the solvent has a miscibility in water of less than 7 wt. %, more preferably less than 5 wt %, and more preferably less than 3 wt %.

In another aspect, the invention pertains to a catheter injectable depot composition and a method of administering such composition as described above, wherein the beneficial agent is selected from a drug, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents, antiproliferative agents, antimitotic agents, angiogenic agents, anticoagulants, fibrinolytic agents, growth factors, antibodies, ocular drugs, and metabolites, analogs, derivatives, fragments, and purified, isolated, recombinant and chemically synthesized versions of these species. In preferred embodiments, the beneficial agent is human growth hormone, methionine-human growth hormone; des-phenylalanine human growth hormone, alpha-, beta- or gamma-interferon, erythropoietin, glucagon, calcitonin, heparin, interleukin-1, interleukin-2, Factor VIII, Factor IX, luteinizing hormone, relaxin, follicle-stimulating hormone, atrial natriuretic factor, filgrastim epidermal growth factors (EGFs), platelet-derived growth factor (PDGFs), insulin-like growth factors (IGFs), fibroblast-growth factors (FGFs), transforming-growth factors (TGFs), interleukins (ILs), colony-stimulating factors (CSFs, MCFs, GCSFs, GMCSFs), Interferons (IFNs), endothelial growth factors (VEGF, EGFs), erythropoietins (EPOs), angiopoietins (ANGs), placenta-derived growth factors (PlGFs), and hypoxia induced transcriptional regulators (HIFs). Preferably, the beneficial agent is present in an amount of from 0.1 to 50% by weight of the combined amounts of the polymer, the solvent and the beneficial agent. In preferred embodiments, the beneficial agent is in the form of particles dispersed or dissolved in the viscous gel, wherein the beneficial agent is in the form of particles having an average particle size of from 0.1 to 250 microns. In certain preferred embodiments, the beneficial agent is in the form of particles, wherein each particle further comprises a component selected from the group consisting of a stabilizing agent, bulking agent, chelating agent and buffering agent.

BRIEF DESCRIPTION OF THE DRAWINGS

The foregoing and other objects, features and advantages of the present invention will be more readily understood upon reading the following detailed description in conjunction with the drawings in which.

DETAILED DESCRIPTION OF THE INVENTION

Overview and Definitions

Figure 1:
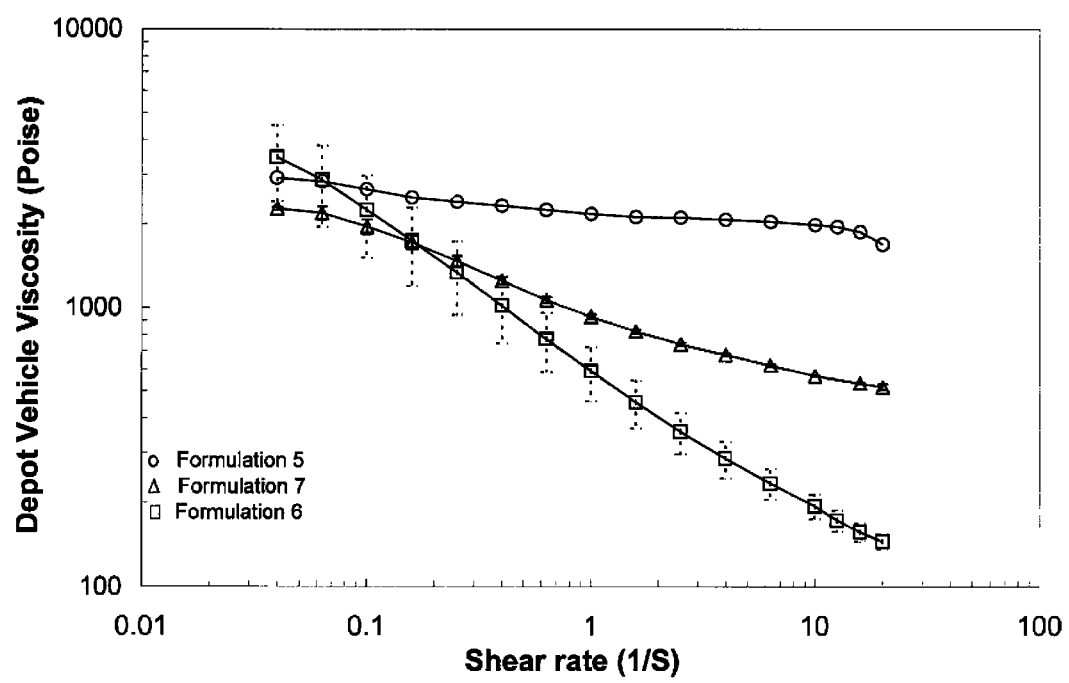
FIG. 1 is a graph illustrating the rheological behavior of depot vehicles formulated with different solvents, i.e., Formulations 5, 6 and 7.

The present invention is directed to an injectable depot composition that serves as an implanted sustained release beneficial agent delivery system after injection into a patient's body. In particular, the present invention pertains to an injectable depot composition that exhibits improved shear thinning behavior and a low injection force. By maintaining high viscosity of the composition at low shear, the intactness of the composition is maintained. The present invention also relates to a method of using the injectable depot composition to administer a beneficial agent to a patient. The injectable depot composition is a gel formed from a bioerodible, biocompatible polymer, a solvent having a miscibility in water of less than or equal to 7% at 25° C.; a thixotropic amount of a thixotropic agent mixed with the polymer solution effective to form a thixotropic composition, the thixotropic agent being selected from the group consisting essentially of lower alkanols and the amount being less than 15 weight percent of the combined weight of the solvent and the thixotropic agent; and a beneficial agent.

The composition provides sustained release of the beneficial agent by restricting water migration from the aqueous environment surrounding the implant system, thus delivering the beneficial agent over a prolonged period of time. Water uptake is controlled by virtue of the water-immiscible aromatic alcohol. Because the polymer of the composition is bioerodible, the implant system does not have to be surgically removed after beneficial agent is depleted from the implant.

Generally, the compositions of the invention are gel-like and form with a substantially homogeneous nonporous structure throughout the implant upon implantation and during drug delivery, even as it hardens. Furthermore, while the polymer gel implant will slowly harden when subjected to an aqueous environment, the hardened implant may maintain a rubbery (nonrigid) composition with the glass transition temperature $T_g$ being below 37° C.

Although the aromatic alcohol in these compositions itself acts as a thixotropic agent, it has been discovered that addition of a thixotropic amount of a thixotropic agent mixed with the polymer solution effective to form a thixotropic composition as described herein, provides an injectable depot composition having surprisingly substantially significantly improved shear thinning behavior and further reduced injection force as compared to previously described depot compositions. In some embodiments, pore formers and solubility modulators of the beneficial agent may be added to the implant systems to provide desired release profiles from the implant systems, along with typical pharmaceutical excipients and other additives that do not change the beneficial aspects of the present invention.

The preferred compositions herein allow beneficial agent to be loaded into the interior of the polymer at levels that are above that required to saturate the beneficial agent in water, thereby facilitating zero order release of beneficial agent.

Additionally, the preferred compositions may provide viscous gels that have a glass transition temperature that is less than 37° C., such that the gel remains nonrigid for a period of time after implantation of 24 hours or more.

In describing and claiming the present invention, the following terminology will be used in accordance with the definitions set out below:

The singular forms "a," "an" and "the" include plural referents unless the context clearly dictates otherwise. Thus, for example, reference to "a solvent" includes a single solvent as well as a mixture of two or more different solvents, reference to "a beneficial agent" includes a single beneficial agent as well as two or more different beneficial agents in combination, reference to "an aromatic alcohol" includes a single aromatic alcohol as well as a mixture of two or more different aromatic alcohols, and the like.

The term "beneficial agent" means an agent that effects a desired beneficial, often pharmacological, effect upon administration to a human or an animal, whether alone or in combination with other pharmaceutical excipients or inert ingredients.

As used herein, the term "polynucleotide" refers to a polymeric form of nucleotides of any length, either ribonucleotides or deoxyribonucleotides, and includes double- or single-stranded DNA and RNA. It also includes known types of modifications, substitutions, and internucleotide modifications, which are known in the art.

As used herein, the term "recombinant polynucleotide" refers to a polynucleotide of genomic, cDNA, semisynthetic, or synthetic origin which, by virtue of its origin or manipulation: is not associated with all or a portion of a polynucleotide with which it is associated in nature; is linked to a polynucleotide other than that to which it is linked in nature; or does not occur in nature.

As used herein, the term "polypeptide" refers to a polymer of amino acids, including, for example, peptides, oligopeptides, and proteins and derivatives, analogs and fragments thereof, as well as other modifications known in the art, both naturally occurring and non-naturally occurring.

As used herein, the terms "purified" and "isolated" when referring to a polypeptide or nucleotide sequence means that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present.

The term "AUC" means the area under the curve obtained from an in vivo assay in a subject by plotting blood plasma concentration of the beneficial agent in the subject against time, as measured from the time of implantation of the composition, to a time "t" after implantation. The time t will correspond to the delivery period of beneficial agent to a subject.

The term "burst index" means, with respect to a particular composition intended for systemic delivery of a beneficial agent, the quotient formed by dividing (i) the AUC calculated for the first time period after implantation of the composition into a subject divided by the number of hours in the first time period ($t_1$), by (ii) the AUC calculated for the time period of delivery of beneficial agent, divided by the number of hours in the total duration of the delivery period ($t_2$). For example the burst index at 24 hours is the quotient formed by dividing (i) the AUC calculated for the first twenty-four hours after implantation of the composition into a subject divided by the number 24, by (ii) the AUC calculated for the time period of delivery of beneficial agent, divided by the number of hours in the total duration of the delivery period.

The phrase "dissolved or dispersed" is intended to encompass all means of establishing a presence of beneficial agent in the gel composition and includes dissolution, dispersion, suspension and the like.

The term "systemic" means, with respect to delivery or administration of a beneficial agent to a subject, that the beneficial agent is detectable at a biologically-significant level in the blood plasma of the subject.

The term "local" means, with respect to delivery or administration of a beneficial agent to a subject, that the beneficial agent is delivered to a localized site in the subject but is not detectable at a biologically significant level in the blood plasma of the subject.

The term "gel vehicle" means the composition formed by mixture of the polymer and solvent in the absence of the beneficial agent.

The term "prolonged period" means a period of time over which release of a beneficial agent from the implant of the invention occurs, which will generally be about one week or longer, and preferably about 30 days or longer.

The term "initial burst" means, with respect to a particular composition of this invention, the quotient obtained by dividing (i) the amount by weight of beneficial agent released from the composition in a predetermined initial period of time after implantation, by (ii) the total amount of beneficial agent that is to be delivered from an implanted composition. It is understood that the initial burst may vary depending on the shape and surface area of the implant. Accordingly, the percentages and burst indices associated with initial burst described herein are intended to apply to compositions tested in a form resulting from dispensing of the composition from a standard syringe.

The term "solubility modulator" means, with respect to the beneficial agent, an agent that will alter the solubility of the beneficial agent, with reference to polymer solvent or water, from the solubility of beneficial agent in the absence of the modulator. The modulator may enhance or retard the solubility of the beneficial agent in the solvent or water. However, in the case of beneficial agents that are highly water soluble, the solubility modulator will generally be an agent that will retard the solubility of the beneficial agent in water. The effects of solubility modulators of the beneficial agent may result from interaction of the solubility modulator with the solvent, or with the beneficial agent itself, such as by the formation of complexes, or with both. For the purposes hereof, when the solubility modulator is "associated" with the beneficial agent, all such interactions or formations as may occur are intended. Solubility modulators may be mixed with the beneficial agent prior to its combination with the viscous gel or may be added to the viscous gel prior to the addition of the beneficial agent, as appropriate.

The terms "subject" and "patient" mean, with respect to the administration of a composition of the invention, an animal or a human being.

Since all solvents, at least on a molecular level, will be soluble in water (i.e., miscible with water) to some very limited extent, the term "immiscible" as used herein means that 7% or less by weight, preferably 5% or less, of the solvent is soluble in or miscible with water. For the purposes of this disclosure, solubility values of solvent in water are considered to be determined at 25° C. Since it is generally recognized that solubility values as reported may not always be conducted at the same conditions, solubility limits recited herein as percent by weight miscible or soluble with water as part of a range or upper limit may not be absolute. For example, if the upper limit on solvent solubility in water is recited herein as "7% by weight," and no further limitations on the solvent are provided, the solvent "triacetin," which has a reported solubility in water of 7.17 grams in 100 ml of water, is considered to be included within the limit of 7%. A solubility limit in water of less than 7% by weight as used herein does not include the solvent triacetin or solvents having solubilities in water equal to or greater than triacetin.

The term "bioerodible" refers to a material that gradually decomposes, dissolves, hydrolyzes and/or erodes in situ. Generally, the "bioerodible" polymers herein are polymers that are hydrolyzable, and bioerode in situ primarily through hydrolysis.

The term "thixotropic" is used in its conventional sense to refer to a gel composition that can liquefy or at least exhibit a decrease in apparent viscosity upon application of mechanical force such as shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A "thixotropic agent" as used herein is one that increases the thixotropy of the composition in which it is contained, promoting shear thinning and enabling use of reduced injection force.

The polymer, solvent and other agents of the invention must be "biocompatible"; that is they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal.

The following definitions apply to the molecular structures described herein:

As used herein, the phrase "having the formula" or "having the structure" is not intended to be limiting and is used in the same way that the term "comprising" is commonly used.

The term "alkyl" as used herein refers to a saturated hydrocarbon group typically, although not necessarily, containing 1 to about 30 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "aryl" as used herein, and unless otherwise specified, refers to an aromatic substituent containing a single aromatic ring or multiple aromatic rings that are fused together, linked covalently, or linked to a common group such as a methylene or ethylene moiety. Preferred aryl groups contain one aromatic ring or two fused or linked aromatic rings, e.g., phenyl, naphthyl, biphenyl, diphenylether, diphenylamine, benzophenone, and the like, and most preferred aryl groups are monocyclic. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the term "aryl" includes heteroaryl, substituted aryl, and substituted heteroaryl groups.

The term "aralkyl" refers to an alkyl group substituted with an aryl group, wherein alkyl and aryl are as defined above. The term "heteroaralkyl" refers to an alkyl group substituted with a heteroaryl group. Unless otherwise indicated, the term "aralkyl" includes heteroaralkyl and substituted aralkyl groups as well as unsubstituted aralkyl groups. Generally, the term "aralkyl" herein refers to an aryl-substituted lower alkyl group, preferably a phenyl substituted lower alkyl group such as benzyl, phenethyl, 1-phenylpropyl, 2-phenylpropyl, and the like.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heterocyclic" refers to a cyclic substituent that is heteroatom-containing, the term "heteroaryl" refers to an aryl substituent that is heteroatom-containing, and the like.

By "substituted" as in "substituted alkyl," "substituted aryl" and the like, as alluded to in some of the aforementioned definitions, is meant that in the alkyl or aryl moiety, respectively, at least one hydrogen atom bound to a carbon atom is replaced with one or more noninterfering substituents such as hydroxyl, alkoxy, thio, amino, halo, and the like.

I. Injectable Depot Compositions:

As described previously, injectable depot compositions for delivery of beneficial agents over a prolonged period of time may be formed as viscous gels prior to injection of the depot into a subject. The viscous gel supports dispersed beneficial agent to provide appropriate delivery profiles, which include those having low initial burst, of the beneficial agent as the beneficial agent is released from the depot over time.

The polymer, solvent and other agents of the invention must be biocompatible, that is, they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal. In certain embodiments, the beneficial agent may be administered locally to avoid or minimize systemic side effects. Gels of the present invention containing a beneficial agent may be injected/implanted directly into or applied as a coating to the desired location, e.g., subcutaneous, intramuscular, intravascular, intramyocardial, adventitial, intratumoral, or intracerebral portion, wound sites, tight joint spaces or body cavity of a human or animal.

Typically, the viscous gel will be injected from a standard hypodermic syringe that has been prefilled with the beneficial agent-viscous gel composition as the depot. It is often preferred that injections take place using the smallest size needle (i.e., smallest diameter) to reduce discomfort to the subject when the injection is in a subcutaneous, intramuscular, intravascular (high/low flow), intramyocardial, adventitial, intratumoral, or intracerebral portion, wound sites, tight joint spaces or body cavity of a human or animal. It is desirable to be able to inject gels through needles ranging from 16 gauge and higher, preferably 20 gauge and higher, more preferably 22 gauge and higher, even more preferably 24 gauge and higher. With highly viscous gels, i.e., gels having a viscosity of about 200 poise or greater, injection forces to dispense the gel from a syringe having a needle in the 20-30 gauge range may be so high as to make the injection difficult or reasonably impossible when done manually. At the same time, the high viscosity of the gel is desirable to maintain the integrity of the depot after injection and during the dispensing period and also facilitate desired suspension characteristics of the beneficial agent in the gel.

A thixotropic gel exhibits reduced viscosity when subjected to shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A composition of a polymer and polymer solvent that includes an agent that imparts thixotropic characteristics to the viscous gel formed by the polymer solvent and polymer provides the desired advantages noted above. It is additionally desirable to use the thixotropic agent in amounts that are sufficiently small so as not to unnecessarily increase the mass and volume of the depot that is to be injected. In this regard it is desirable that the thixotropic agent, i.e., lower alkanols, particularly ethanol, is not a polymer solvent. As is described more fully below, the addition of small amounts of lower alkanols, especially ethanol, to polymer depots formed as viscous gels from lactic acid-based polymers and suitable polymer solvents provide the foregoing desirable characteristics in compositions of the invention described here.

A. The Bioerodible, Biocompatible Polymer

Polymers that are useful in conjunction with the methods and compositions of the invention are bioerodible, i.e., they gradually hydrolyze, dissolve, physically erode, or otherwise disintegrate within the aqueous fluids of a patient's body. Generally, the polymers bioerode as a result of hydrolysis or physical erosion, although the primary bioerosion process is typically hydrolysis.

Such polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polyhydroxycellulose, chitin, chitosan, hyaluronic acid, and copolymers, terpolymers and mixtures thereof.

Presently preferred polymers are polylactides, that is, a lactic acid-based polymer that can be based solely on lactic acid or can be a copolymer based on lactic acid and glycolic acid and/or caprolactone, which may include small amounts of other comonomers that do not substantially affect the advantageous results that can be achieved in accordance with the present invention. As used herein, the term "lactic acid" includes the isomers L-lactic acid, D-lactic acid, DL-lactic acid and lactide, while the term "glycolic acid" includes glycolide. Most preferred are polymers selected from the group consisting of polylactide polymers, commonly referred to as PLA, poly(lactide-co-glycolide)copolymers, commonly referred to as PLGA, and poly(caprolactone-co-lactic acid) (PCL-co-LA). The polymer may have a monomer ratio of lactic acid/glycolic acid of from about 100:0 to about 15:85, preferably from about 75:25 to about 30:70, more preferably from about 60:40 to about 40:60, and an especially useful copolymer has a monomer ratio of lactic acid/glycolic acid of about 50:50.

The poly(caprolactone-co-lactic acid) (PCL-co-LA) polymer has a comonomer ratio of caprolactone/lactic acid of from about 10:90 to about 90:10, from about 50:50; preferably from about 35:65 to about 65:35; and more preferably from about 25:75 to about 75:25. In certain embodiments, the lactic acid-based polymer comprises a blend of about 0-90% caprolactone, about 0-100% lactic acid, and about 0-60% glycolic acid.

The lactic acid-based polymer has an average molecular weight of from about 1,000 to about 120,000, preferably from about 5,000 to about 50,000, more preferably from about 8,000 to about 30,000, as determined by gel permeation chromatography (GPC). In contrast to prior polymer-based injectable depots, the present invention allows use of higher molecular weight polymers, insofar as the aromatic alcohol of the composition provides excellent shear thinning even with high molecular weight polymers. As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 8,000, 10,000, 30,000 and 100,000 are available from Boehringer Ingelheim Chemicals, Inc. (Petersburg, Va.), Medisorb Technologies International L.P. (Cincinnati, Ohio) and Birmingham Polymers, Inc. (Birmingham, Ala.) as described below.

Examples of polymers include, but are not limited to, Poly (D,L-lactide) Resomer® L104, PLA-L104, Poly (D,L-lactide-co-glycolide) 50:50 Resomer® RG502, Poly (D,L-lactide-co-glycolide) 50:50 Resomer® RG502H, Poly (D,L-lactide-co-glycolide) 50:50 Resomer® RG503, Poly (D,L-lactide-co-glycolide) 50:50 Resomer® RG506, Poly L-Lactide MW 2,000 (Resomer® L 206, Resomer® L 207, Resomer® L 209, Resomer® L 214); Poly D,L Lactide (Resomer® R 104, Resomer® R 202, Resomer® R 203, Resomer® R 206, Resomer® R 207, Resomer® R 208); Poly L-Lactide-co-D,L-lactide 90:10 (Resomer® LR 209); Poly glycolide (Resomer® G 205); Poly D,L-lactide-co-glycolide 50:50 (Resomer® RG 504 H, Resomer® RG 504, Resomer® RG 505); Poly D-L-lactide-co-glycolide 75:25 (Resomer® RG 752, Resomer® RG755, Resomer® RG 756); Poly D,L-lactide-co-glycolide 85:15 (Resomer® RG 858); Poly L-lactide-co-trimethylene carbonate 70:30 (Resomer® LT 706); Poly dioxanone (Resomer® X 210) (Boehringer Ingelheim Chemicals, Inc., Petersburg, Va.).

Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

The biocompatible polymer is present in the gel composition in an amount ranging from about 5 to about 90% by weight, preferably from about 10 to about 85% by weight, preferably from about 15 to about 80% by weight, preferably from about 20 to about 75% by weight, preferably from about 30 to about 70% by weight and typically from about 35 to about 65% by weight of the viscous gel, the viscous gel comprising the combined amounts of the biocompatible polymer and a solvent having a miscibility in water that is less than 7 wt. % at 25° C. The solvent will be added to polymer in amounts described below, to provide implantable or viscous gels. Again, the combination of the solvent and the thixotropic agent described herein enables a much wider range of polymer/solvent ratios than obtainable previously.

B. Solvents

The injectable depot composition of the invention contains a water-immiscible solvent having a miscibility in water that is less than 7 wt. % at 25° C., in addition to the bioerodible polymer, the thixotropic agent and the beneficial agent. Preferably, the compositions described herein are also free of solvents having a miscibility in water that is greater than 7 wt. % at 25° C.

The solvent must be biocompatible, should form a viscous gel with the polymer, and restrict water uptake into the implant. Suitable solvents will substantially restrict the uptake of water by the implant and, as noted above, may be characterized as immiscible in water, i.e., having a solubility or miscibility in water of at most 7% by weight. Preferably, the water solubility of the aromatic alcohol is 5 wt. % or less, more preferably 3 wt. % or less, and even more preferably 1 wt. % or less. Most preferably, the solubility of the aromatic alcohol in water is equal to or less than 0.5 weight percent. In preferred embodiments, the solvent is selected from the group consisting of an aromatic alcohol, esters of aromatic acids, aromatic ketones, and mixtures thereof.

Water miscibility may be determined experimentally as follows: Water (1-5 g) is placed in a tared clear container at a controlled temperature, about 25° C., and weighed, and a candidate solvent is added dropwise. The solution is swirled to observe phase separation. When the saturation point appears to be reached, as determined by observation of phase separation, the solution is allowed to stand overnight and is rechecked the following day. If the solution is still saturated, as determined by observation of phase separation, then the percent (w/w) of solvent added is determined. Otherwise, more solvent is added and the process is repeated. Solubility or miscibility is determined by dividing the total weight of solvent added by the final weight of the solvent/water mixture. When solvent mixtures are used, they are premixed prior to adding to the water.

The aromatic alcohol has the structural formula (I)

$$\text{Ar-(L)}_n\text{-OH} \qquad (I)$$

wherein Ar is a substituted or unsubstituted aryl or heteroaryl group, n is zero or 1, and L is a linking moiety. Preferably, Ar is a monocyclic aryl or heteroaryl group, optionally substituted with one or more noninterfering substituents such as hydroxyl, alkoxy, thio, amino, halo, and the like. More preferably, Ar is an unsubstituted 5- or 6-membered aryl or heteroaryl group such as phenyl, cyclopentadienyl, pyridinyl, pyrimadinyl, pyrazinyl, pyrrolyl, pyrazolyl, imidazolyl, furanyl, thiophenyl, thiazolyl, isothiazolyl, or the like. The subscript "n" is zero or 1, meaning that the linking moiety L may or may not be present. Preferably, n is 1 and L is generally a lower alkylene linkage such as methylene or ethylene, wherein the linkage may include heteroatoms such as O, N or S. Most preferably, Ar is phenyl, n is 1, and L is methylene, such that the aromatic alcohol is benzyl alcohol.

The aromatic acid ester or ketone must be biocompatible, should form a viscous gel with the polymer, and restrict water uptake into the implant. Like the aromatic alcohol, suitable aromatic acid esters and ketones will substantially restrict the uptake of water by the implant and, as noted above, may be characterized as immiscible in water, i.e., having a solubility or miscibility in water of at most 7% by weight. Preferably, the water solubility of the solvent alcohol is 5 wt. % or less, more preferably 3 wt. % or less, and even more preferably 1 wt. % or less. Most preferably, the solubility of the solvent in water is equal to or less than 0.5 weight percent.

The aromatic acid ester or ketone may be selected from the lower alkyl and aralkyl esters of aromatic acids, and aryl and aralkyl ketones. Generally, although not necessarily, the aromatic acid esters and ketones will respectively have the structural formula (II) or (III)

In the ester of formula (II), $R^1$ is substituted or unsubstituted aryl, aralkyl, heteroaryl or heteroaralkyl, preferably substituted or unsubstituted aryl or heteroaryl, more preferably monocyclic or bicyclic aryl or heteroaryl optionally substituted with one or more noninterfering substituents such as hydroxyl, carboxyl, alkoxy, thio, amino, halo, and the like, still more preferably 5- or 6-membered aryl or heteroaryl such as phenyl, cyclopentadienyl, pyridinyl, pyrimadinyl, pyrazinyl, pyrrolyl, pyrazolyl, imidazolyl, furanyl, thiophenyl, thiazolyl, or isothiazolyl, and most preferably 5- or 6-membered aryl. $R^2$ is hydrocarbyl or heteroatom-substituted hydrocarbyl, typically lower alkyl or substituted or unsubstituted aryl, aralkyl, heteroaryl or heteroaralkyl, preferably lower alkyl or substituted or unsubstituted aralkyl or heteroaralkyl, more preferably lower alkyl or monocyclic or bicyclic aralkyl or heteroaralkyl optionally substituted with one or more noninterfering substituents such as hydroxyl, carboxyl, alkoxy, thio, amino, halo, and the like, still more preferably lower alkyl or 5- or 6-membered aralkyl or heteroaralkyl, and most preferably lower alkyl or 5- or 6-membered aryl optionally substituted with one or more additional ester groups having the structure —O—(CO)—$R^1$. The most preferred esters are benzoic acid and phthalic acid derivatives.

In the ketone of formula (III), $R^3$ and $R^4$ may be selected from any of the $R^1$ and $R^2$ groups identified above.

Art recognized benzoic acid derivatives from which solvents having the requisite solubility may be selected include, without limitation: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, isodecyl benzoate, neopentyl glycol dibenzoate, glyceryl tribenzoate, pentaerylthritol tetrabenzoate, cumylphenyl benzoate, trimethyl pentanediol dibenzoate.

Art recognized phthalic acid derivatives from which solvents having the requisite solubility may be selected include: Alkyl benzyl phthalate, bis-cumyl-phenyl isophthalate, dibutoxyethyl phthalate, dimethyl phthalate, dimethyl phthalate, diethyl phthalate, dibutyl phthalate, diisobutyl phthalate, butyl octyl phthalate, diisoheptyl phthalate, butyl octyl phthalate, diisononyl phthalate, nonyl undecyl phthalate, dioctyl phthalate, di-isooctyl phthalate, dicapryl phthalate, mixed alcohol phthalate, di-(2-ethylhexyl)phthalate, linear heptyl nonyl phthalate, linear heptyl nonyl undecyl phthalate, linear nonyl phthalate, linear nonyl undecyl phthalate, linear dinonyl, didecyl phthalate (diisodecyl phthalate), diundecyl phthalate, ditridecyl phthalate, undecyldodecyl phthalate, decyltridecyl phthalate, blend (50/50) of dioctyl and didecyl phthalates, butyl benzyl phthalate, and dicyclohexyl phthalate.

Most preferred solvents are derivatives of benzoic acid and include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred.

The composition may also include, in addition to the water-immiscible solvent(s), one or more additional miscible solvents ("component solvents"), provided that any such additional solvent is other than a lower alkanol. Component solvents compatible and miscible with the primary solvent(s) may have a higher miscibility with water and the resulting mixtures may still exhibit significant restriction of water uptake into the implant. Such mixtures will be referred to as "component solvent mixtures." Useful component solvent mixtures may exhibit solubilities in water greater than the primary solvents themselves, typically between 0.1 weight percent and up to and including 50 weight percent, preferably up to and including 30 weight percent, and most preferably up to and including 10 weight percent, without detrimentally affecting the restriction of water uptake exhibited by the implants of the invention.

Component solvents useful in component solvent mixtures are those solvents that are miscible with the primary solvent or solvent mixture, and include, but are not limited to, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, and 1-dodecylazacyclo-heptan-2-one, and mixtures thereof.

The solvent or solvent mixture is capable of dissolving the polymer to form a viscous gel that can maintain particles of the beneficial agent dissolved or dispersed and isolated from the environment of use prior to release. The compositions of the present invention provide implants having a low burst index. Water uptake is controlled by the use of a solvent or component solvent mixture that solubilizes or plasticizes the polymer but substantially restricts uptake of water into the implant.

The solvent or solvent mixture is typically present in an amount of from about 95 to about 5% by weight, preferably about 75 to about 15% by weight, and most preferably about 65% to about 20% by weight of the viscous gel. In certain embodiments, the solvent comprises a mixture of the aromatic alcohol (formula I), aromatic acid ester (formula II) and ketone (formula III). In an especially preferred embodiment, the solvent is selected from an aromatic alcohol, lower alkyl and aralkyl esters of benzoic acid. Presently, the most preferred solvents are benzyl alcohol, benzyl benzoate and the lower alkyl esters of benzoic acid, preferably ethyl benzoate. Generally, the weight ratio of the aromatic alcohol to the ester or ketone is in the range of about 1% to about 99%, preferably in the range of about 10% to about 90%, more preferably in the range of about 20% to about 80%, even more preferably in the range of about 25% to about 75%, and often in the range of about 50%.

The viscous gel formed by mixing the polymer and the solvent typically exhibits a viscosity of from about 100 to about 200,000 poise, preferably from about 500 to about 50,000 poise, often from about 1,000 to about 50,000 poise measured at a 1 sec$^{-1}$ shear rate and 25° C. using a Haake Rheometer at about 1-2 days after mixing is completed. Mixing the polymer with the solvent can be achieved with conventional low shear equipment such as a Ross double planetary mixer for from about 10 minutes to about 1 hour, although shorter and longer periods may be chosen by one skilled in the art depending on the particular physical characteristics of the composition being prepared. Since it is often desirable to administer the implant as an injectable composition, a countervailing consideration when forming implants that are viscous gels is that the polymer, solvent, thixotropic agent and beneficial agent composition have sufficiently low viscosity in order to permit it to be forced through a small diameter, e.g., 16 gauge and higher, preferably 20 gauge and higher, more preferably 22 gauge and higher, and even more preferably, 24 gauge and higher, needle. If necessary, adjustment of viscosity of the gel for injection can be accomplished with emulsifying agents as described herein. Yet, such compositions should have adequate dimensional stability so as to remain localized and be able to be removed if necessary. The particular gel or gel-like compositions of the present invention satisfy such requirements.

C. Thixotropic Agents

The thixotropic agent, i.e., an agent that imparts thixotropic properties to the polymer gel, is selected from the lower alkanols. Lower alkanol means an alcohol that contains 2-6 carbon atoms and is straight chain or branched chain. Such alcohols may be exemplified by ethanol, isopropanol, and the like. Importantly, such a thixotropic agent is not a polymer solvent. (See, e.g., *Development of an in situ forming biodegradable poly-lactide-co-glycolide system for controlled release of proteins*, Lambert, W. J., and Peck, K. D., *Journal of Controlled Release,* 33 (1995)189-195).

It has been discovered that addition of a thixotropic amount of a thixotropic agent to the polymer solution of the polymer and polymer solvent provides an injectable depot composition having surprisingly substantially significantly improved shear thinning behavior and further reduced injection force as compared to previously described depot compositions. Surprisingly, only a very small amount of thixotropic agent needs to be added to the polymer solution of the polymer and polymer solvent to obtain the desired reduction in injection force when the gel is dispensed from a syringe. Accordingly, an amount of thixotropic agent that is less than 15% by weight of the combined weight of the polymer solvent and the thixotropic agent has been found to be satisfactory. The thixotropic agent may be present in amounts of 0.01 to 15 weight percent, preferably in amounts of 0.1 to 5 weight percent, and often in amounts of 0.5 to 5 weight percent of the combined weight of the solvent and the thixotropic agent.

It is to be understood that the thixotropic agent of the present invention does not constitute a mere diluent or a polymer-solvent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the thixotropic agent so that once injected into place, the thixotropic agent has little impact on the release properties of the original system. Preferably, the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of 12 or less, preferably 8 or less.

D. Beneficial Agent

The beneficial agent can be any physiologically or pharmacologically active substance or substances optionally in combination with pharmaceutically acceptable carriers and additional ingredients such as antioxidants, stabilizing agents, permeation enhancers, etc. that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, a drug, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents including anti-inflammatory corticosteroids, antiproliferative agents, antimitotic agents, angiogenic agents, anticoagulants, fibrinolytic agents, growth factors, antibodies, ocular drugs, and metabolites, analogs (including synthetic and substituted analogs), derivatives (including aggregative conjugates/fusion with other macromolecules and covalent conjugates with unrelated chemical moieties by means known in the art) fragments, and purified, isolated, recombinant and chemically synthesized versions of these species.

Examples of drugs that may be delivered by the composition of the present invention include, but are not limited to, procaine, procaine hydrochloride, tetracaine, tetracaine hydrochloride, cocaine, cocaine hydrochloride, chloroprocaine, chloroprocaine hydrochloride, proparacaine, proparacaine hydrochloride, piperocaine, piperocaine hydrochloride, hexylcaine, hexylcaine hydrochloride, naepaine, naepaine hydrochloride, benzoxinate, benzoxinate hydrochloride, cyclomethylcaine, cyclomethylcaine hydrochloride, cyclomethylcaine sulfate, lidocaine, lidocaine hydrochloride, bupivacaine, bupivacaine hydrochloride, mepivacaine, mepivacaine hydrochloride, prilocalne, prilocalne hydrochloride, dibucaine and dibucaine hydrochloride, etidocaine, benzocaine, propoxycaine, dyclonin, pramoxine, oxybuprocaine, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isofluorophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth factors such as epidermal growth factors (EGF), platelet-derived growth factors (PDGF), fibroblast growth factors (FGF), transforming growth factors-α (TGF-α), transforming growth factors-β (TGF-β), erythropoietin (EPO), insulin-like growth factor-I (IGF-I), insulin-like growth factor-II (IGF-II), interleukin-1, interleukin-2, interleukin-6, interleukin-8, tumor necrosis factor-α (TNF-α), tumor necrosis factor-β (TNF-β), Interferon-α (INF-α), Interferon-β (INF-β), Interferon-γ (INF-γ), Interferon-ω (INF-ω), colony stimulating factors (CGF), vascular cell growth factor (VEGF), thrombopoietin (TPO), stromal cell-derived factors (SDF), placenta growth factor (PIGF), hepatocyte growth factor (HGF), granulocyte macrophage colony stimulating factor (GM-CSF), glial-derived neurotropin factor (GDNF), granulocyte colony stimulating factor (G-CSF), ciliary neurotropic factor (CNTF), bone morphogenic proteins (BMP), coagulation factors, human pancreas hormone releasing factor, analogs and derivatives of these compounds, and pharmaceutically acceptable salts of these compounds, or their analogs or derivatives.

Additional examples of drugs that may be delivered by the composition of the present invention include, but are not limited to, antiproliferative/antimitotic agents including natural products such as vinca alkaloids (i.e., vinblastine, vincristine, and vinorelbine), paclitaxel, epidipodophyllotoxins (i.e., etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as $G(GP)II_bIII_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide hormones (i.e., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory, such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives, i.e., aspirin; para-aminophenol derivatives, i.e., acetominophen) indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligonucleotides and combinations thereof; cell cycle inhibitors, mTOR inhibitors, and growth factor signal transduction kinase inhibitors, analogs and derivatives of these compounds, and pharmaceutically acceptable salts of these compounds, or their analogs or derivatives.

In certain preferred embodiments, the beneficial agent includes chemotactic growth factors, proliferative growth factors, stimulatory growth factors, and transformational peptide growth factors including genes, precursors, post-translational-variants, metabolites, binding-proteins, receptors, receptor agonists and antagonists of the following growth factor families: epidermal growth factors (EGFs), platelet-derived growth factor (PDGFs), insulin-like growth factors (IGFs), fibroblast-growth factors (FGFs), transforming-growth factors (TGFs), interleukins (ILs), colony-stimulating factors (CSFs, MCFs, GCSFs, GMCSFs), Interferons (IFNs), endothelial growth factors (VEGF, EGFs), erythropoietins (EPOs), angiopoietins (ANGs), placenta-derived growth factors (PIGFs), and hypoxia induced transcriptional regulators (HIFs).

The present invention also finds application with chemotherapeutic agents for the local application of such agents to avoid or minimize systemic side effects. Gels of the present invention containing chemotherapeutic agents may be injected directly into the tumor tissue for sustained delivery of the chemotherapeutic agent over time. In some cases, particularly after resection of the tumor, the gel may be implanted directly into the resulting cavity or may be applied to the remaining tissue as a coating. In cases in which the gel is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as, for example, cisplatin and carboplatin and the water soluble derivatives of paclitaxel. Those characteristics of the invention that minimize the burst effect are particularly advantageous in the administration of water soluble beneficial agents of all kinds, but particularly those compounds that are clinically useful and effective but may have adverse side effects.

To the extent not mentioned above, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microencapsulate or process into microspheres can be incorporated into the compositions of the present invention without the level of degradation caused by exposure to high temperatures and denaturing solvents often present in other processing techniques.

The beneficial agent is preferably incorporated into the viscous gel formed from the polymer and the solvent in the form of particles typically having an average particle size of from about 0.1 to about 250 microns, preferably from about 1 to about 200 microns and often from 30 to 125 microns. For instance, particles having an average particle size of about 5 microns have been produced by spray drying or freeze drying an aqueous mixture containing 50% sucrose and 50% chicken lysozyme (on a dry weight basis) and mixtures of 10-20% hGH and 15-30 mM zinc acetate. Such particles have been used in certain of the examples illustrated in the figures. Conventional lyophilization processes can also be utilized to form particles of beneficial agents of varying sizes using appropriate freezing and drying cycles.

To form a suspension or dispersion of particles of the beneficial agent in the viscous gel formed from the polymer and the solvent, any conventional low shear device can be used such as a Ross double planetary mixer at ambient conditions. In this manner, efficient distribution of the beneficial agent can be achieved substantially without degrading the beneficial agent.

The beneficial agent is typically dissolved or dispersed in the composition in an amount of from about 0.1% to about 50% by weight, preferably in an amount of from about 1% to about 40%, more preferably in an amount of about 2% to about 30%, and often 2 to 20% by weight of the combined amounts of the polymer, solvent, and beneficial agent. Depending on the amount of beneficial agent present in the composition, one can obtain different release profiles and burst indices. More specifically, for a given polymer and solvent, by adjusting the amounts of these components and the amount of the beneficial agent, one can obtain a release profile that depends more on the degradation of the polymer than the diffusion of the beneficial agent from the composition or vice versa. In this respect, at lower beneficial agent loading rates, one generally obtains a release profile reflecting degradation of the polymer wherein the release rate increases with time. At higher loading rates, one generally obtains a release profile caused by diffusion of the beneficial agent wherein the release rate decreases with time. At intermediate loading rates, one obtains combined release profiles so that if desired, a substantially constant release rate can be attained. In order to minimize burst, loading of beneficial agent on the order of 30% or less by weight of the overall gel composition, i.e., polymer, solvent and beneficial agent, is preferred, and loading of 20% or less is more preferred.

Release rates and loading of beneficial agent will be adjusted to provide for therapeutically effective delivery of the beneficial agent over the intended sustained delivery period. Preferably, the beneficial agent will be present in the polymer gel at concentrations that are above the saturation concentration of beneficial agent in water to provide a drug reservoir from which the beneficial agent is dispensed. While the release rate of beneficial agent depends on the particular circumstances, such as the beneficial agent to be administered, release rates on the order of from about 0.1 micrograms/day to about 30 milligrams/day, preferably from about 1 microgram/day to about 20 milligrams per day, more preferably from about 10 micrograms/day to about 10 milligrams/day, for periods of from about 24 hours to about 180 days, preferably 24 hours to about 120 days, more preferably 24 hours to about 90 days, and often 3 days to about 90 days can be obtained.

Further, the dose of beneficial agent may be adjusted by adjusting the amount of depot gel injected. Greater amounts may be delivered if delivery is to occur over shorter periods. Generally, higher release rate is possible if a greater burst can be tolerated. In instances where the gel composition is surgically implanted, or used as a "leave behind" depot when surgery to treat the disease state or another condition is concurrently conducted, it is possible to provide higher doses than would normally be administered if the implant was injected. Further, the dose of beneficial agent may be controlled by adjusting the volume of the gel implanted or the injectable gel injected. Preferably, the system releases 40% or less by weight of the beneficial agent present in the viscous gel within the first 24 hours after implantation in the subject. More preferably, 30% or less by weight of the beneficial agent will be released within the first 24 hours after implantation, and the implanted composition has a burst index of 12 or less, and preferably 8 or less.

Optional Additional Components

Other components may be present in the gel composition, to the extent they are desired or provide useful properties to the composition, such as polyethylene glycol, hydroscopic agents, stabilizing agents (for example, surfactants like tween 20, tween 80, and the like, sugars such as sucrose, treholose, and the like, salts, antioxidants), pore forming agents, bulking agents (such as sorbitol, mannitol, glycine, and the like), chelating agents (such as divalent metal ions including zinc, magnesium, calcium, copper and the like), buffering agents (such as phosphate, acetane, succinate, histidine, TRIS, and the like) and others. When the composition includes a peptide or a protein that is soluble in, or unstable in, an aqueous environment, it may be highly desirable to include a solubility modulator that may, for example, be a stabilizing agent, in the composition. Various modulating agents are described in U.S. Pat. Nos. 5,654,010 and 5,656,297, the disclosures of which are incorporated herein by reference. In the case of hGH, for example, it is preferable to include an amount of a salt of a divalent metal, preferably zinc. Examples of such modulators and stabilizing agents, which may form complexes with the beneficial agent or associate to provide the stabilizing or modulated release effect, include metal cations, preferably divalent, present in the composition as magnesium carbonate, zinc carbonate, calcium carbonate, magnesium acetate, magnesium sulfate, zinc acetate, zinc sulfate, zinc chloride, magnesium chloride, magnesium oxide, magnesium hydroxide, other antacids, and the like. The amounts of such agents used will depend on the nature of the complex formed, if any, or the nature of the association between the beneficial agent and the agent. Molar ratios of solubility modulator or stabilizing agent to beneficial agent of about 100:1 to 1:1, preferably 10:1 to 1:1, typically can be utilized.

Pore forming agents include biocompatible materials that when contacted with body fluids dissolve, disperse or degrade to create pores or channels in the polymer matrix. Typically, organic and nonorganic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Utility and Administration

The means of administration of the implants is not limited to injection, although that mode of delivery may often be preferred. Where the implant will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

Compositions of this invention without beneficial agent are useful for wound healing, bone repair and other structural support purposes.

To further understand the various aspects of the present invention, the results set forth in the previously described figures were obtained in accordance with the following examples.

Example 1

A gel vehicle for use in an injectable depot of the composition was prepared as follows. A glass vessel was tared on a Mettler PJ3000 top loader balance. Poly (D,L-lactide-co-glycolide) (PLGA), available as 50:50 Resomer® RG502

(PLGA RG 502), was weighed into the glass vessel. The glass vessel containing PLGA was tared and the corresponding solvent was added. Amounts expressed as percentages for various polymer/solvent combinations are set forth in Table 1, below. The polymer/solvent mixture was manually stirred with a stainless steel square-tip spatula, resulting in a sticky amber paste-like substance containing white polymer particles. The vessel containing the polymer/solvent mixture was sealed and placed in a temperature controlled incubator equilibrated to 39° C. The polymer/solvent mixture was removed from the incubator when it appeared to be a clear amber homogeneous gel. Incubation time intervals ranged from 1 to 4 days, depending on solvent and polymer type and solvent and polymer ratios.

Thereafter, the mixture was placed in an oven (65° C.) for 30 minutes. It was noted that the PLGA-504 was dissolved in the mixture upon removal from the oven.

Additional depot gel vehicles are prepared with the following solvents or mixtures: benzyl benzoate, benzyl alcohol, propylene glycol, and ethanol and the following polymers: Poly (D,L-lactide) Resomer® L104, PLA-L104, Poly (D,L-lactide-co-glycolide) 50:50 Resomer® RG502, Poly (D,L-lactide-co-glycolide) 50:50 Resomer® RG502H, Poly (D,L-lactide-co-glycolide) 50:50 Resomer® RG503, Poly L-Lactide MW 2,000 (Resomer® L 206, Resomer® L 207, Resomer® L 209, Resomer® L 214); Poly D,L Lactide (Resomer® R 104, Resomer® R 202, Resomer® R 203, Resomer® R 206, Resomer® R 207, Resomer® R 208); Poly L-Lactide-co-D,L-lactide 90:10 (Resomer® LR 209); Poly D-L-lactide-co-glycolide 75:25 (Resomer® RG 752, Resomer® RG755, Resomer® RG 756); Poly D,L-lactide-co-glycolide 85:15 (Resomer® RG 858); Poly L-lactide-co-trimethylene carbonate 70:30 (Resomer® LT 706); Poly dioxanone (Resomer® X 210) (Boehringer Ingelheim Chemicals, Inc., Petersburg, Va.); DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.). Representative gel vehicles are described in Table 1 below.

TABLE 1

| Formulation | Polymer gm (%) | Benzyl Benzoate gm (%) | Benzyl Alcohol gm (%) | Propylene Glycol gm (%) |
|---|---|---|---|---|
| 1 | 5.0365 | 4.5093 | 0.5178 | — |
| 2 | 5.0139 | 3.7553 | 1.2560 | — |
| 3 | 5.0350 | 4.5193 | — | 0.5206 |
| 4 | 5.0024 | 3.7547 | — | 1.2508 |
| 5 | 5.0068 | 5.0044 | — | — |

Example 2

Rheological behavior was tested for depot vehicles formulated with different solvents. A vehicle comprising 50 wt. % polymer (PLGA RG502) and 50 wt. % solvent (benzyl alcohol) was prepared according to the procedures outlined in Example 1. For comparative purposes, solvent comprising benzyl benzoate (e.g., formulation 5) or benzyl benzoate combined with ethanol (e.g., formulation 7) were also prepared. Table 2 lists the formulations used in the test.

TABLE 2

| Formulation | Polymer (%) | Benzyl Benzoate (%) | Benzyl Alcohol (%) | Ethanol (%) |
|---|---|---|---|---|
| 5 | 50.0 | 50.0 | 0.0 | 0.0 |
| 6 | 50.0 | 0.0 | 50.0 | 0.0 |
| 7 | 45.0 | 52.8 | 0.0 | 2.2 |

Formulations 5, 6 and 7 were tested for viscosity under various shear rates. As indicated in FIG. 1, significant shear thinning behavior was observed when benzyl alcohol was used as the solvent (e.g., formulation 6), in contrast to formulations using benzyl benzoate (e.g., formulation 5) and benzyl benzoate with ethanol as a thixotropic agent (e.g., formulation 7), respectively.

Example 3

Figure 2:
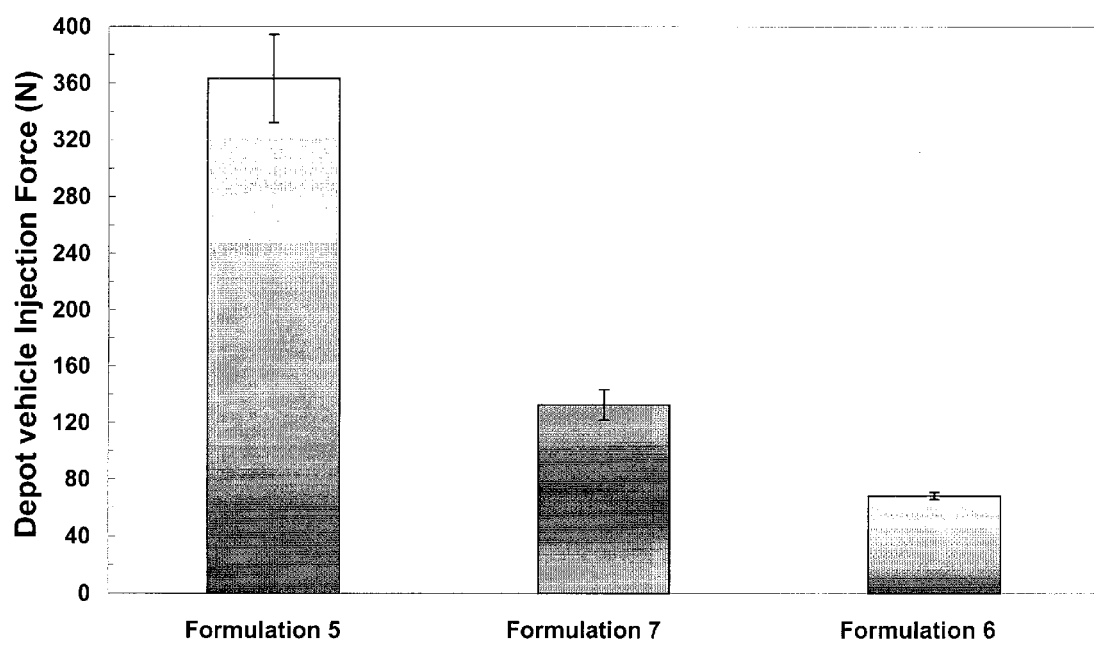
FIG. 2 is a graph illustrating the injection force required to dispense the Formulations 5, 6 and 7 from a 24-gauge needle at 1 ml/minute, at room temperature.

The injection force required to dispense depot vehicles was evaluated for the three formulations identified in Example 2. The formulations were injected through a 24-gauge needle at 1 ml/minute, at room temperature. As indicated in FIG. 2, significantly reduced injection force was observed when benzyl alcohol is used as the solvent (e.g., formulation 6), in contrast to formulations using benzyl benzoate (e.g., formulation 5) and benzyl benzoate with ethanol as a thixotropic agent (e.g., formulation 7), respectively. Notably, due to the shear-thinning behavior, the formulations using benzyl alcohol as the solvent (e.g., formulation 6), and benzyl benzoate with ethanol as a thixotropic agent (e.g., formulation 7) showed significantly reduced injection force while maintaining viscosities equal to or greater than the formulations using benzyl benzoate (e.g., formulation 5), at lower shear rate; thus maintaining the intactness of the depot after injection into the animals.

Example 4

Figure 3:
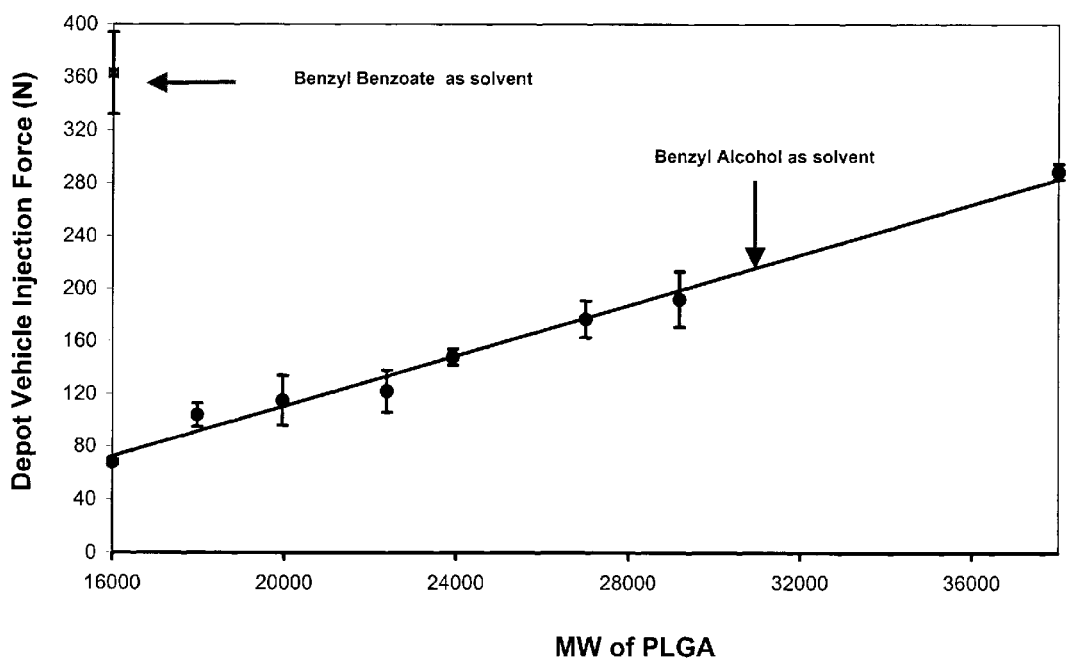
FIG. 3 is a graph illustrating the injection force required to dispense injectable depot compositions formulated with varying poly(lactide-co-glycolide) average molecular weights in combination with benzyl benzoate or benzyl alcohol from a 24-gauge needle at 1 ml/minute, at room temperature.
Figure 4:
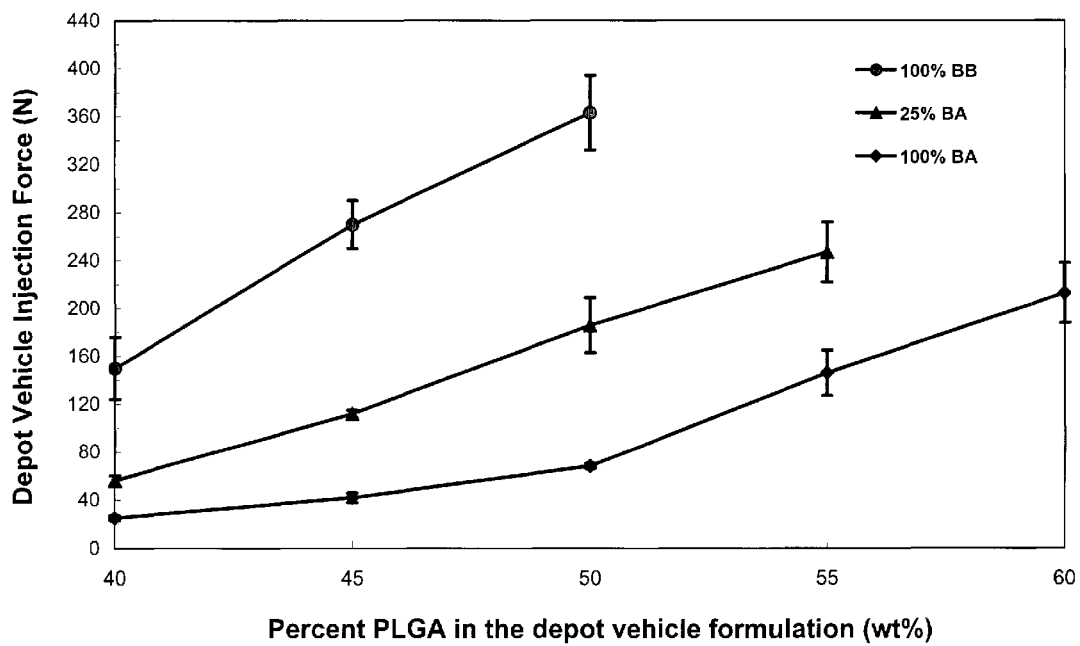
FIG. 4 is a graph illustrating the injection force required to dispense depot compositions formulated with varying poly(lactide-co-glycolide) average molecular weights in combination with benzyl benzoate or benzyl alcohol or mixtures thereof from a 24-gauge needle at 1 ml/minute, at room temperature.

The injection force required to dispense depot vehicles was evaluated for a series of vehicles. Formulations containing PLGA RG502 at various weight percents were each combined with solvents as follows: 100% benzyl benzoate 75 wt. % benzyl benzoate, 25 wt. % benzyl alcohol; and 100% benzyl alcohol. The amount of the solvent was added to bring the total amount of the formulation to 100%, e.g., if PLGA-502 was used at 45 wt. %, 55 wt. % of the solvent was used. The formulations were then tested for the injection force necessary to pass the formulation through a 24-gauge needle at 1 ml/minute, at room temperature. As seen in FIG. 3, benzyl alcohol offers flexibility for depot vehicle formulation, thereby enabling the formulation of depot vehicles with much higher PLGA molecular weights while maintaining reasonably low injection force as compared to similar benzyl benzoate-containing formulations. Furthermore, for any given percentage of PLGA-502 in the formulation, the injection force decreases as the percentage of the benzyl alcohol increases, as illustrated in FIG. 4.

Example 5

Figure 5:
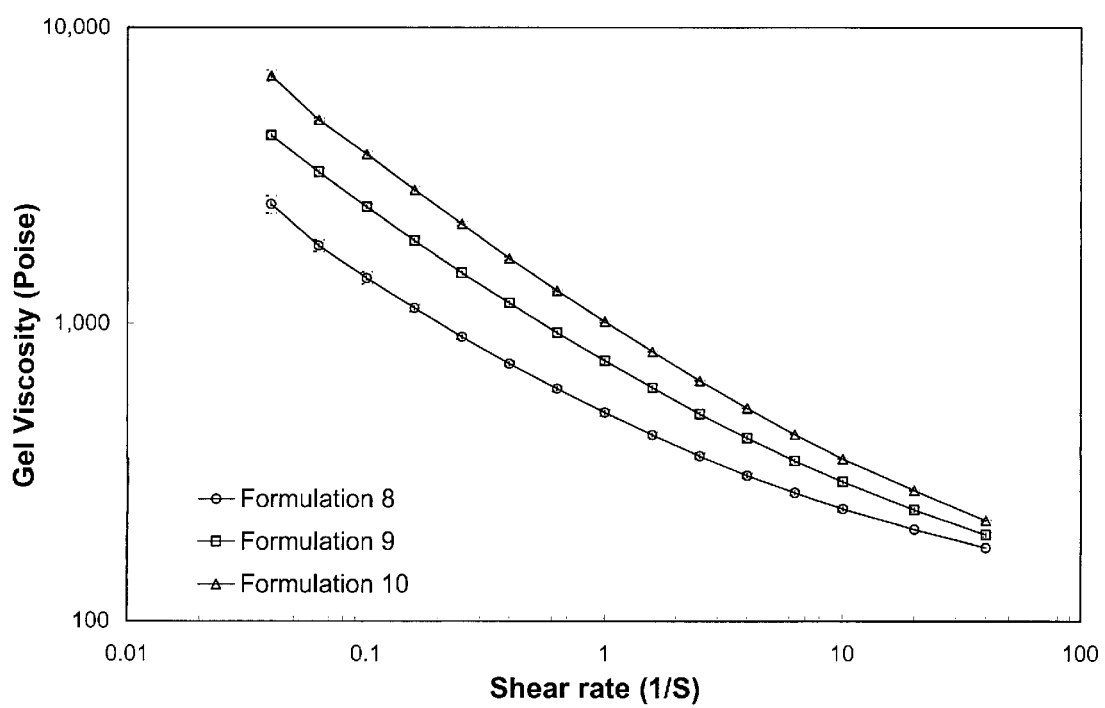
FIG. 5 is a graph illustrating the rheological behavior of depot vehicles formulated with different solvents, i.e., Formulations 8, 9 and 10.

Rheological behavior was tested for depot vehicles formulated with the ethanol as a thixotropic agent alone with benzyl alcohol as described in this invention. The vehicle formulations comprising 50 wt. % polymer (PLGA RG502) and benzyl alcohol as the solvent with 5 and 10% ethanol as a thixotropic agent (e.g., formulations 9 and 10), respectively, were prepared according to the procedures outlined in Example 1. For comparative purposes, solvent comprising only benzyl alcohol (e.g., formulation 8) was also prepared. Table 3 lists the formulations used in the test. Formulations 8, 9 and 10 were tested for viscosity under various shear rates. As indicated in FIG. 5, more significant shear thinning behavior was observed when ethanol was used as a thixotropic agent together with the solvent benzyl alcohol (e.g., formulations 9 and 10), as compared to the formulation using benzyl alcohol alone (e.g., formulation 8).

TABLE 3

| Formulation | Polymer (%)[1] | Benzyl Benzoate (%) | Benzyl Alcohol (%) | Ethanol (%) |
|---|---|---|---|---|
| 8 | 50.0 | 0.0 | 50.0 | 0.0 |
| 9 | 50.0 | 0.0 | 47.5 | 2.5 |
| 10 | 50.0 | 0.0 | 45.0 | 5.0 |

[1]= PLGA RG502 polymer (MW 16,1000)

Example 6

Figure 6:
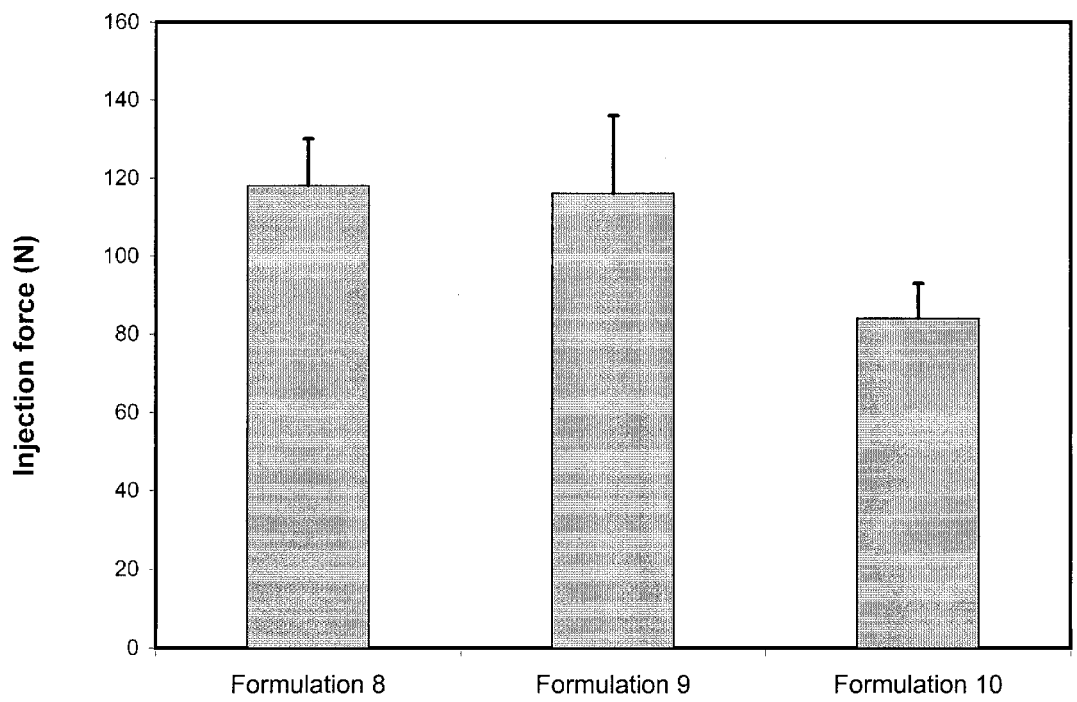
FIG. 6 is a graph illustrating the injection force required to dispense various depot compositions, i.e., Formulations 8, 9 and 10, from a 24-gauge needle at 1 ml/minute, at room temperature.

The injection force required to dispense depot vehicles was evaluated for the three formulations identified in Example 5. The formulations were injected through a 24-gauge needle at 1 ml/minute, at room temperature. As indicated in FIG. 6, further reduced injection force was observed when ethanol is used as a thixotropic agent together with the solvent benzyl alcohol (e.g., formulations 9 and 10), as compared to formulations using benzyl alcohol alone (e.g., formulation 8).

Example 7

Rheological behavior was tested for depot vehicles formulated with ethanol as a thixotropic agent together with the mixture of benzyl benzoate and benzyl alcohol as described in this invention. The vehicle formulations comprising 50 wt. % polymer (PLGA RG502) and the mixture of benzyl benzoate and benzyl alcohol as the solvent with 5 and 10% ethanol as a thixotropic agent (e.g., formulations 12-15), respectively, were prepared according to the procedures outlined in Example 1. For comparative purposes, the mixture of solvent without ethanol as a thixotropic agent (e.g., formulation 11) was also prepared. Table 4 lists the formulations used in the test.

Figure 7:
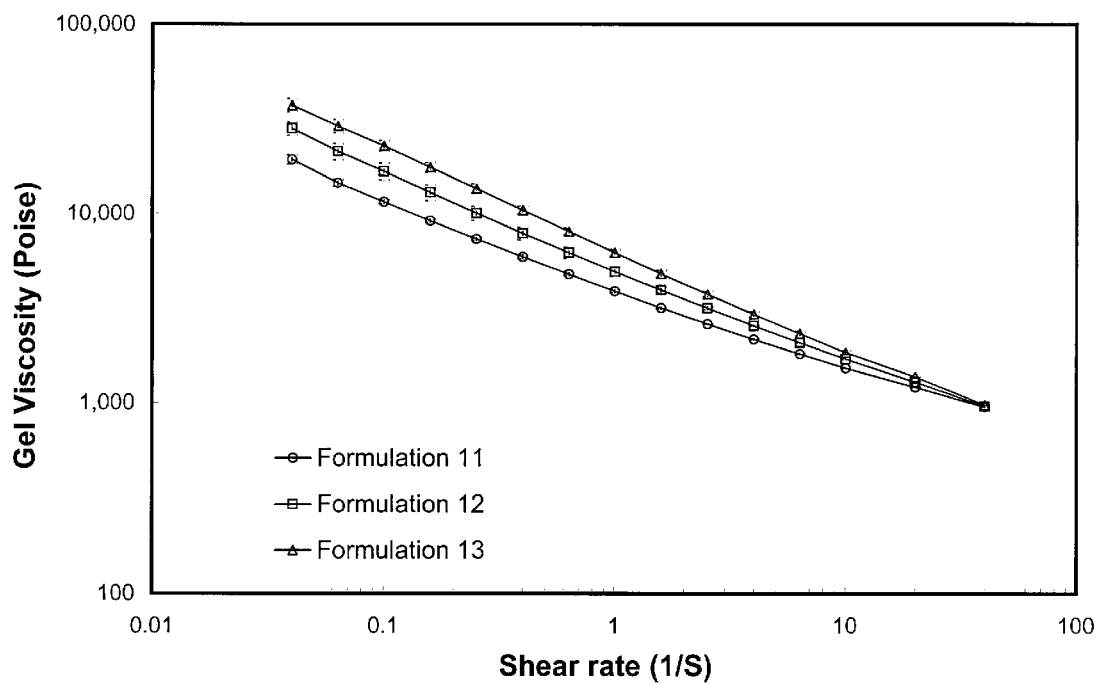
FIG. 7 is a graph illustrating the rheological behavior of depot vehicles formulated with different solvents, i.e., Formulations 11, 12 and 13.
Figure 8:
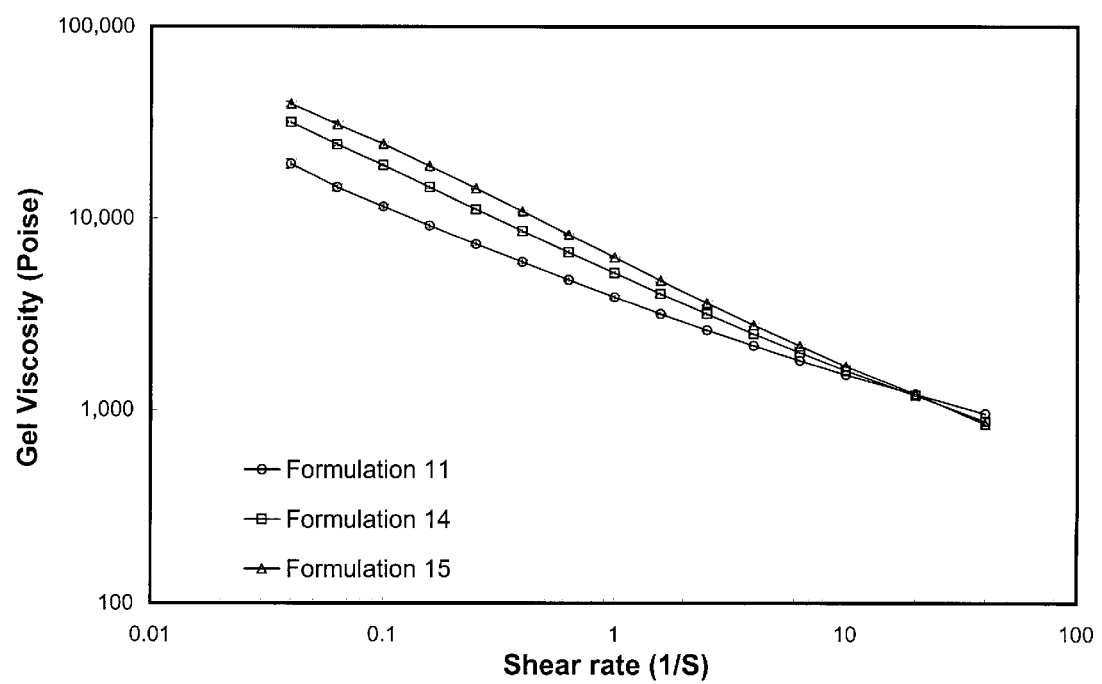
FIG. 8 is a graph illustrating the rheological behavior of depot vehicles formulated with different solvents, i.e., Formulations 11, 14 and 15.

Formulations 11-15 were tested for viscosity under various shear rates. As indicated in FIGS. 7 and 8, more significant shear thinning behavior was observed when ethanol was used as a thixotropic agent together with the mixture of benzyl benzoate and benzyl alcohol as solvent (e.g., formulations 12 and 13 in FIG. 7 and formulations 14 and 15 in FIG. 8), as compared to the formulation using the mixture of benzyl benzoate and benzyl alcohol without ethanol as a thixotropic agent (e.g., formulation 11).

TABLE 4

| Formulation | Polymer (%)[1] | Benzyl Benzoate (%) | Benzyl Alcohol (%) | Ethanol (%) |
|---|---|---|---|---|
| 11 | 50.0 | 37.5 | 12.5 | 0.0 |
| 12 | 50.0 | 35.6 | 11.9 | 2.5 |
| 13 | 50.0 | 33.7 | 11.3 | 5.0 |
| 14 | 50.0 | 37.5 | 10.0 | 2.5 |
| 15 | 50.0 | 37.5 | 7.5 | 5.0 |

[1]= PLGA RG502 polymer (MW 16,000).

Example 8

Figure 9:
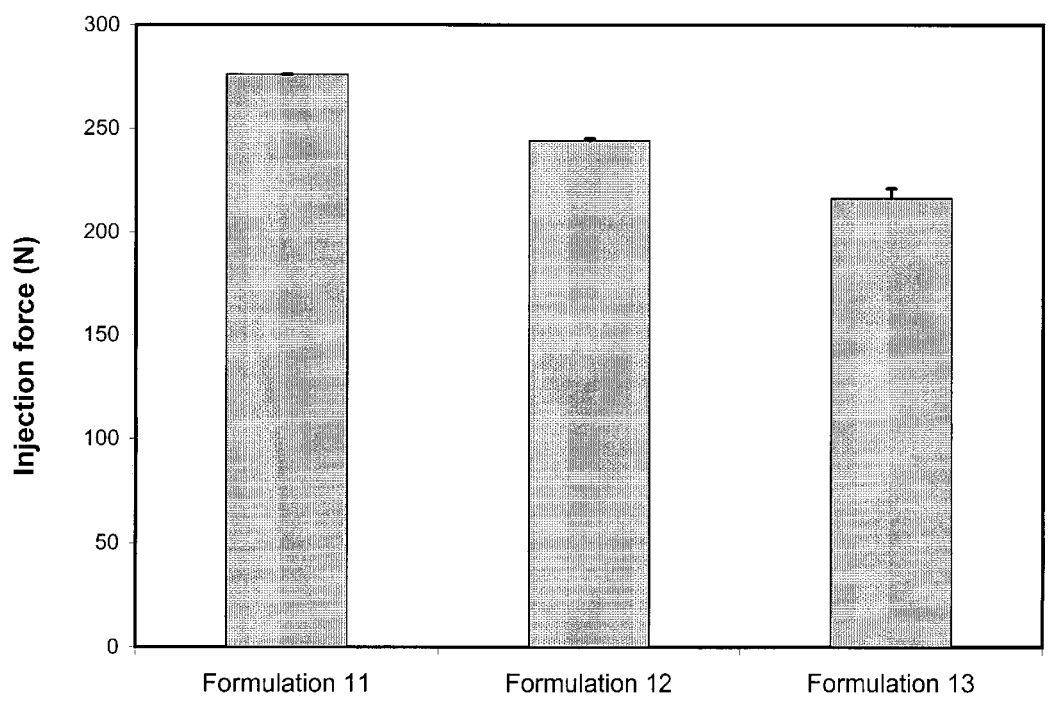
FIG. 9 is a graph illustrating the injection force required to dispense various depot compositions, i.e., Formulations 11, 12 and 13, from a 24-gauge needle at 1 ml/minute, at room temperature.
Figure 10:
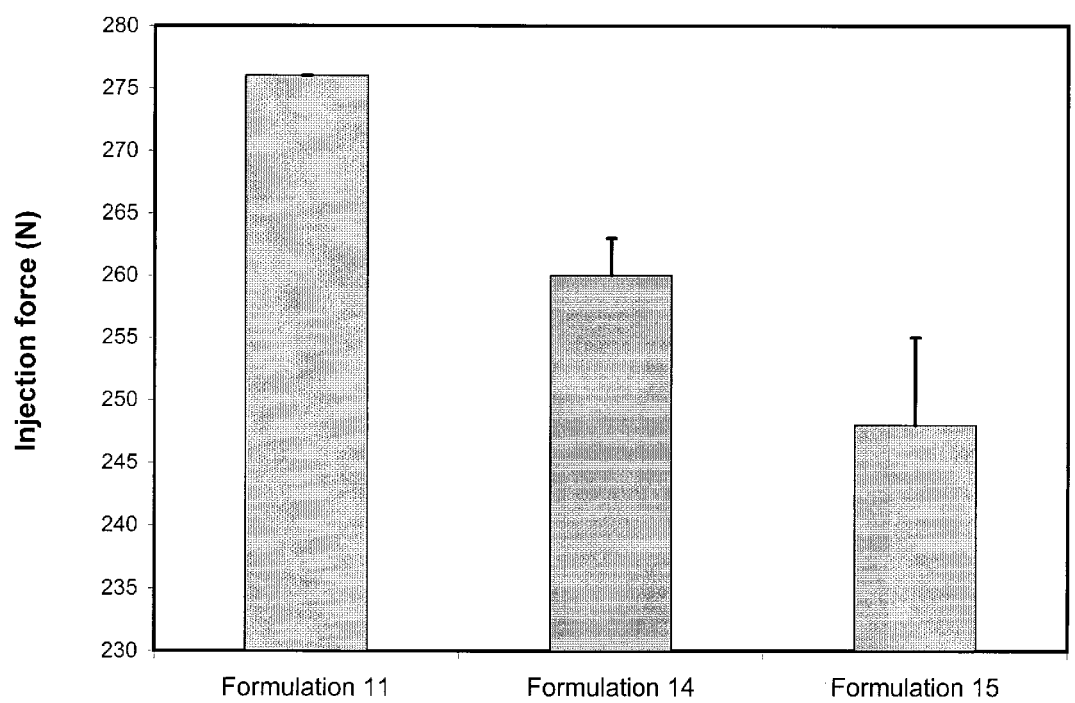
FIG. 10 is a graph illustrating the injection force required to dispense various depot compositions, i.e., Formulations 11, 14 and 15, from a 24-gauge needle at 1 ml/minute, at room temperature.

The injection force required to dispense depot vehicles was evaluated for the three formulations identified in Example 7. The formulations were injected through a 24-gauge needle at 1 ml/minute, at room temperature. As indicated in FIGS. 9 and 10, further reduced injection force was observed when ethanol is used as a thixotropic agent together with the mixture of benzyl benzoate and benzyl alcohol as the solvent (e.g., formulations 12 and 13 in FIG. 9 and formulations 14 and 15 in FIG. 10), as compared to the formulation using the mixture without ethanol as a thixotropic agent (e.g., formulation 11). Due to the shear-thinning behavior, the formulations with benzyl alcohol as a solvent and/or ethanol as a thixotropic agent showed significantly reduced injection force while maintaining equal to or greater than the formulations with benzyl benzoate alone at lower shear rate, thus maintaining the intactness of the depot after injection into the animals.

Example 9 hGH Particle Preparation

Human growth hormone (hGH) particles (optionally containing zinc acetate) were prepared as follows:

hGH solution (5 mg/ml) solution in water (BresaGen Corporation, Adelaide, Australia) was concentrated to 10 mg/mL using a Concentration/Dialysis Selector diafiltering apparatus. The diafiltered hGH solution was washed with 5 times volume of tris or phosphate buffer solution (pH 7.6). Particles of hGH were then formed by spray drying or lyophilization using conventional techniques. Phosphate buffer solutions (5 or 50 mM) containing hGH (5 mg/mL) (and optionally various levels of zinc acetate (0 to 30 mM) when Zn complexed particles were prepared) were spray-dried using a Yamato Mini Spray dryer set at the following parameters:

| Spray Dryer Parameter | Setting |
|---|---|
| Atomizing Air | 2 psi |
| Inlet Temperature | 120° C. |
| Aspirator Dial | 7.5 |
| Solution Pump | 2-4 |
| Main Air Valve | 40-45 psi | hGH particles having a size range between 2-100 microns were obtained.

Lyophilized particles were prepared from tris buffer solutions (5 or 50 mM: pH 7.6) containing hGH (5 mg/mL) using a Durastop μP Lyophilizer in accordance with the following freezing and drying cycles:

| | |
|---|---|
| Freezing cycle | Ramp down at 2.5° C./min to −30° C. and hold for 30 min |
| | Ramp down at 2.5° C./min to −30° C. and hold for 30 min |
| Drying cycle | Ramp up at 0.5° C./min to 10° C. and hold for 960 min |
| | Ramp up at 0.5° C./min to 20° C. and hold for 480 min |
| | Ramp up at 0.5° C./min to 25° C. and hold for 300 min |
| | Ramp up at 0.5° C./min to 30° C. and hold for 300 min |
| | Ramp up at 0.5° C./min to 5° C. and hold for 5000 min |

Example 10 hGH-Stearic Acid Particle Preparation

Human growth hormone (hGH) particles were prepared as follows: Lyophilized hGH (3.22 grams, Pharmacia-Upjohn, Stockholm, Sweden) and stearic acid (3.22 grams, 95% pure, Sigma-Aldrich Corporation, St. Louis, Mo.) were blended and ground. The ground material was compressed in a 13 mm round die, with a force of 10,000 pounds for 5 minutes. Compressed tablets were ground and sieved through a 70 mesh screen followed by a 400 mesh screen to obtain particles having a size range between 38-212 microns.

Example 11

Bupivacaine-Stearic Acid Particle Preparation

Bupivacaine particles were prepared as follows: Bupivacaine hydrochloride (100 grams, Sigma-Aldrich Corporation, St. Louis, Mo.) was sieved through 63-125 micron sieves. The bupivacaine particles and stearic acid (100 grams, 95% pure, Sigma-Aldrich Corporation, St. Louis, Mo.) were blended and ground. The ground material was compressed in a 13 mm round die, with a force of 5,000 pounds for 5 minutes. Compressed tablets were ground and sieved through a 120 mesh screen followed by a 230 mesh screen to obtain particles having a size range between 63-125 microns.

Example 12

Drug Loading

Compressed particles comprising beneficial agent/stearic acid prepared as above are added to a gel vehicle in an amount of 10-20% by weight and blended manually until the dry powder is wetted completely. Then, the milky light yellow particle/gel mixture is thoroughly blended by conventional mixing using a Caframo mechanical stirrer with an attached square-tip metal spatula. Resulting formulations are illustrated in Table 5 below. Final homogenous gel formulations were transferred to 3, 10 or 30 cc disposable syringes for storage or dispensing.

TABLE 5

| Formulation | Polymer (%) | Benzyl Benzoate (%) | Benzyl Alcohol (%) | Ethanol (%) |
|---|---|---|---|---|
| 16[a] | 45.0[1] | 45.0 | 0.0 | 0.0 |
| 17[a] | 39.6[1] | 49.5 | 0.0 | 0.9 |
| 18[a] | 45.0[1] | 33.8 | 11.3 | 0.0 |
| 19[a] | 45.0[2] | 33.8 | 11.3 | 0.0 |
| 20[b] | 58.5[3] | 31.5 | 0.0 | 0.0 |
| 21[b] | 53.5[3] | 0.0 | 31.5 | 0.0 |
| 22[b] | 67.5[3] | 0.0 | 22.5 | 0.0 |
| 23[b] | 67.5[4] | 0.0 | 22.5 | 0.0 |
| 24[c] | 60.0[4] | 0.0 | 20.0 | 0.0 |
| 25[a] | 45.0[1] | 0.0 | 45.0 | 0.0 |

[1] = PLGA RG-502 polymer (MW 16,000);
[2] = PLGA-L/G 50/50 polymer (MW 22,600);
[3] = PLGA L/G 50/50 with ester end group (MW 8,000);
[4] = PLGA L/G 50/50 with acid end group (MW 10,000);
[a] = 5% hGH, 5% SA;
[b] = 10% bupivacaine;
[c] = 10% bupivacaine, 10% SA.

A representative number of implantable gels were prepared in accordance with the foregoing procedures and tested for in vitro release of beneficial agent as a function of time and also in in vivo studies in rats to determine release of the beneficial agent as determined by blood serum or plasma concentrations of beneficial agent as a function of time.

Example 13 hGH In Vivo Studies

In vivo studies in rats were performed following an open protocol to determine serum levels of hGH upon systemic administration of hGH via the implant systems of this invention. Depot gel hGH formulations were loaded into customized 0.5 cc disposable syringes. Disposable 18-gauge 1" needles were attached to the syringes and were heated to 37° C. using a circulator bath. Depot gel hGH formulations were injected into immunosuppressed rats and serum samples were collected post-injection at 1 hour, 4 hours, day 1, 2, 4, 7, 10, 14, 21 and 28. All serum samples were stored at 4° C. prior to analysis. Samples were analyzed for intact hGH content using a radio immuno assay (RIA). At the end of the study, the rats were euthanized for gross clinical observation and the depot was retrieved for intactness observations.

Figure 11:
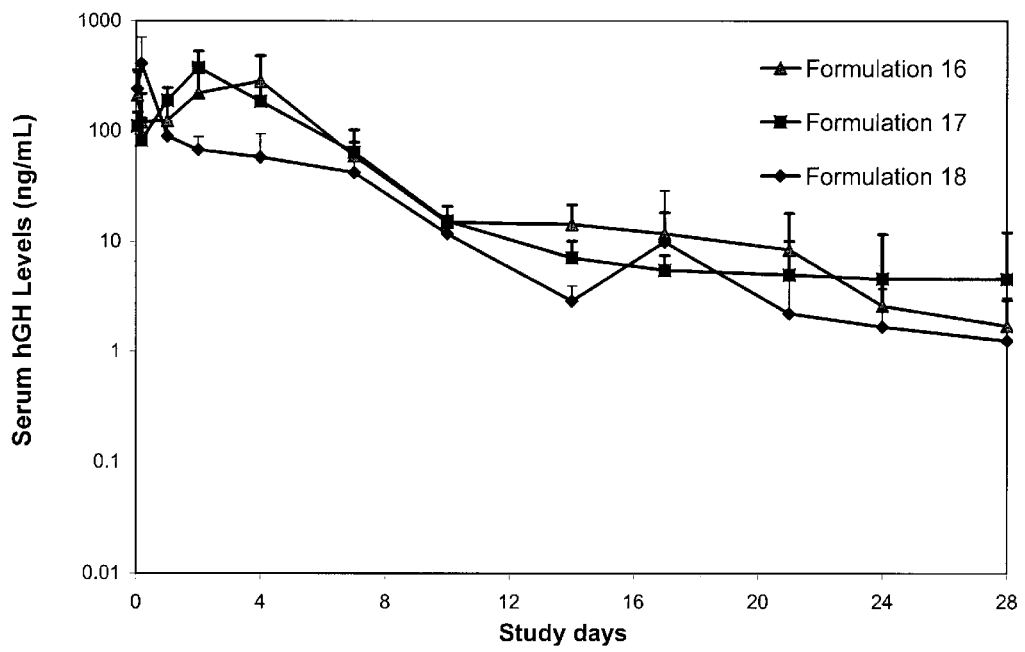
FIG. 11 is a graph illustrating the in vivo release profile of human growth hormone ("hGH") obtained from various depot compositions, including those of the present invention (Formulations 16-18).
Figure 12:
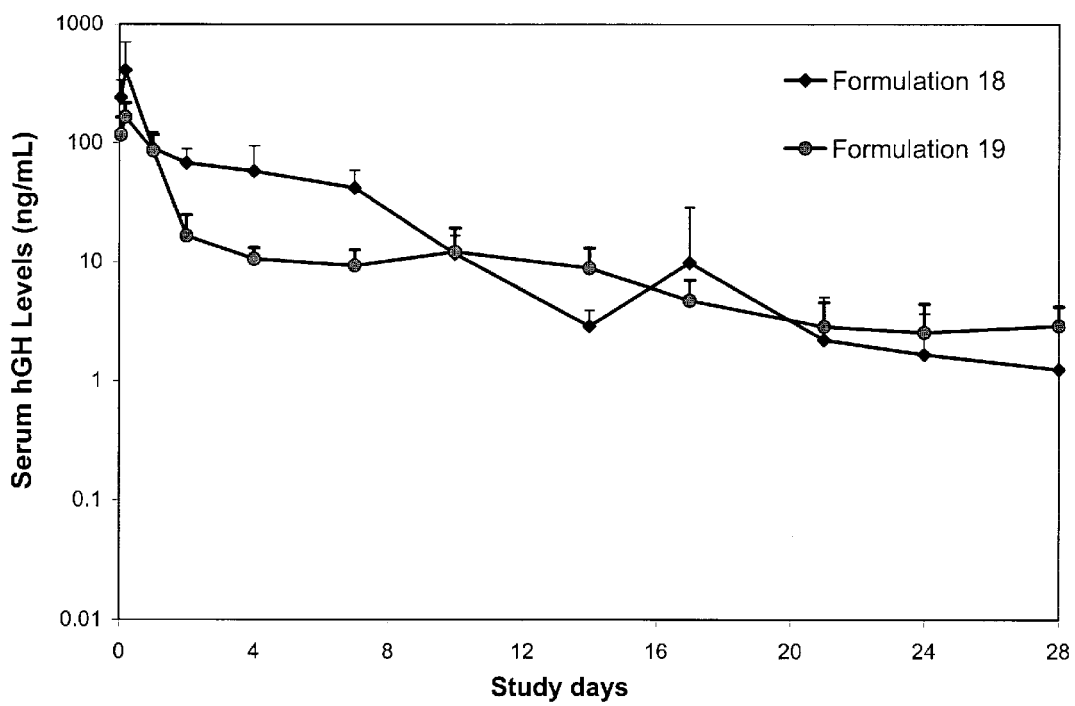
FIG. 12 is a graph illustrating the in vivo release profile of human growth hormone ("hGH") obtained from various depot compositions (Formulations 18 and 19).

FIGS. 11 and 12 illustrate representative in vivo release profiles of hGH obtained in rats from various depot compositions, including those of the present invention. The in vivo release profile of the depot formulations with benzyl alcohol (e.g., formulations 18 and 19) are comparable to the control formulations (without benzyl alcohol, e.g., formulations 16 and 17). Thus, the depot compositions of the present invention reduce the injection force significantly without compromising the in vivo release profile of the beneficial agent.

At the end of the study (i.e., at day 28), the depots were retrieved from the rats. Generally, a one-piece intact round-shaped depot was recovered corresponding to each injected depot in the animal.

Example 14

Bupivacaine In Vivo Studies

In vivo studies in rats (4 per group) were performed following an open protocol to determine plasma levels of bupivacaine upon systemic administration of bupivacaine via the implant systems of this invention. Depot gel bupivacaine formulations were loaded into customized 0.5 cc disposable syringes. Disposable 18-gauge needles were attached to the syringes and were heated to 37° C. using a circulator bath. Depot gel bupivacaine formulations were injected into rats and blood was drawn at specified time intervals (1 hour, 4 hours and on days 1, 2, 5, 7, 9 and 14) and analyzed for bupivacaine using LC/MS. At the end of the study (i.e., at day 14), the rats were euthanized for gross clinical observation and the depot was retrieved for intactness observations.

Figure 13:
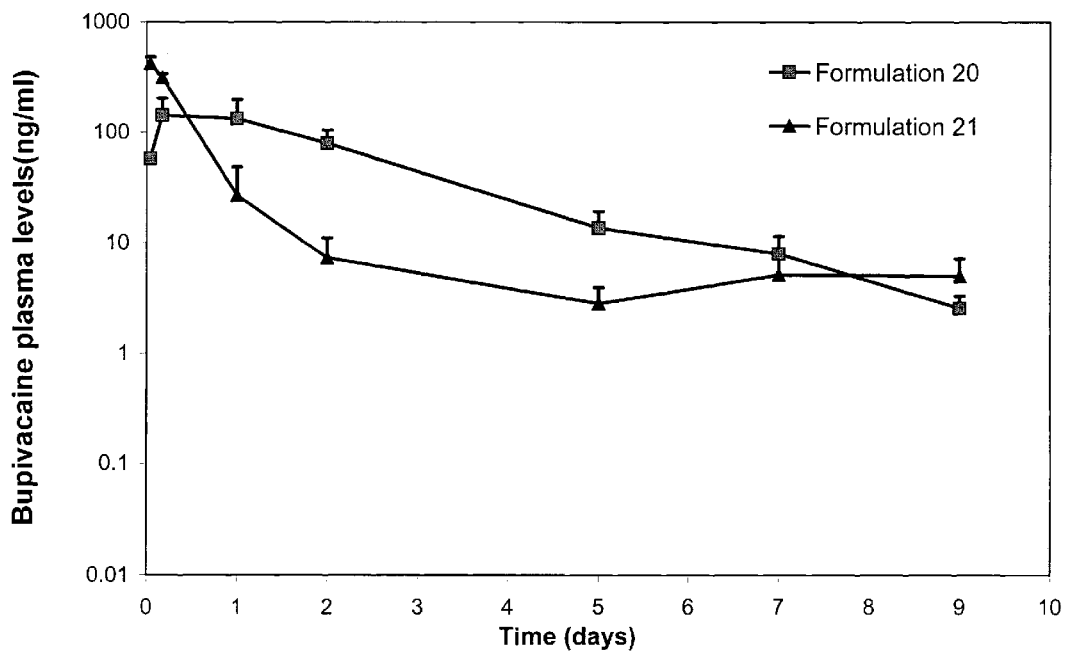
FIG. 13 is a graph illustrating the in vivo release profile of bupivacaine obtained from various depot compositions, including those of the present invention (Formulations 20 and 21).
Figure 14:
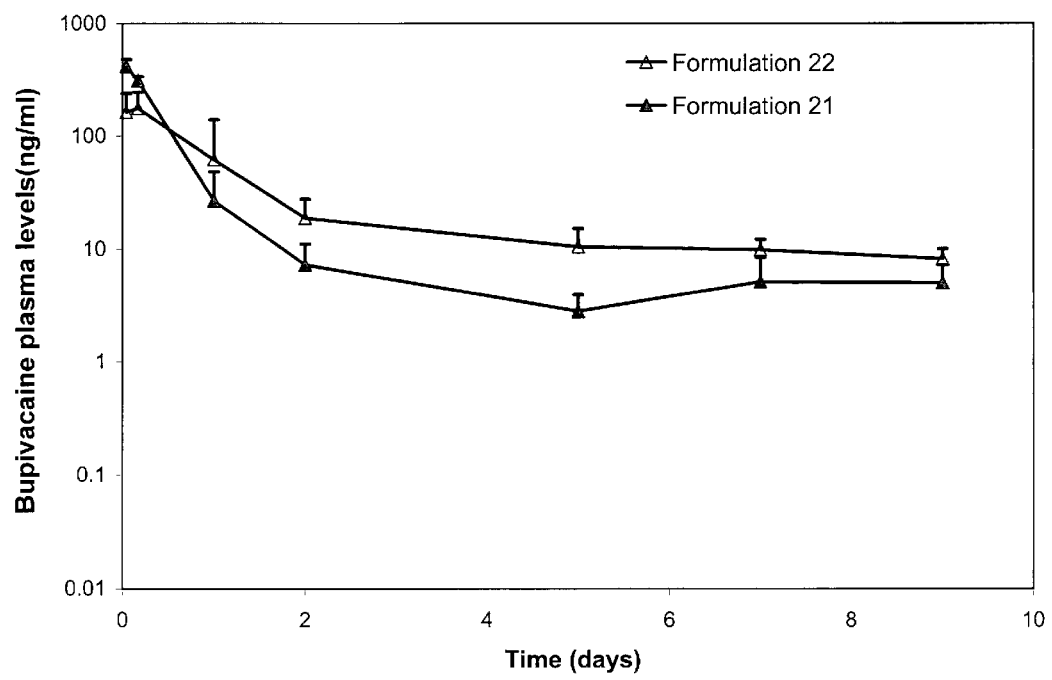
FIG. 14 is a graph illustrating the in vivo release profile of bupivacaine obtained from various depot compositions, including those of the present invention (Formulations 22 and 21).
Figure 15:
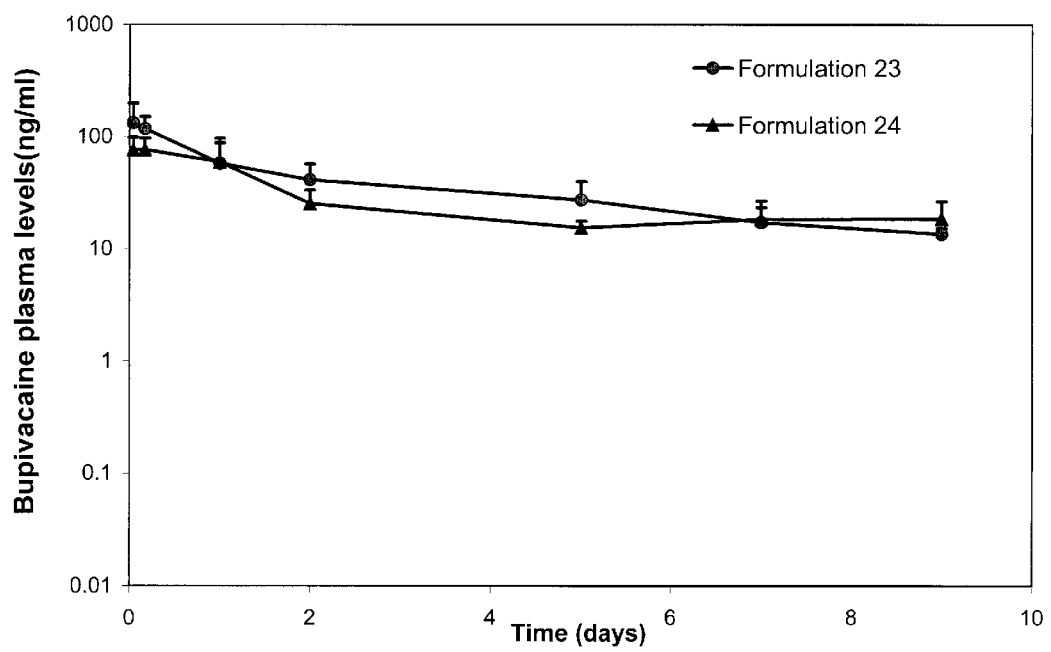
FIG. 15 is a graph illustrating the in vivo release profile of bupivacaine obtained from depot compositions, including those of the present invention (Formulations 23 and 24).

FIGS. 13, 14 and 15 illustrate representative in vivo release profiles of bupivacaine obtained in rats from various depot compositions, including those of the present invention. The in vivo release profiles of the depot formulations with benzyl alcohol are comparable to the control formulations (without benzyl alcohol). Thus, the depot compositions of the present invention reduce the injection force significantly without compromising the in vivo release profile of the beneficial agent.

At the end of the study (i.e., at day 14), the depots were retrieved from the rats. Generally, a one-piece intact round-shaped depot was recovered corresponding to each injected depot in the animal.

Example 15

Stability of hGH in the Depot Formulations

Figure 16:
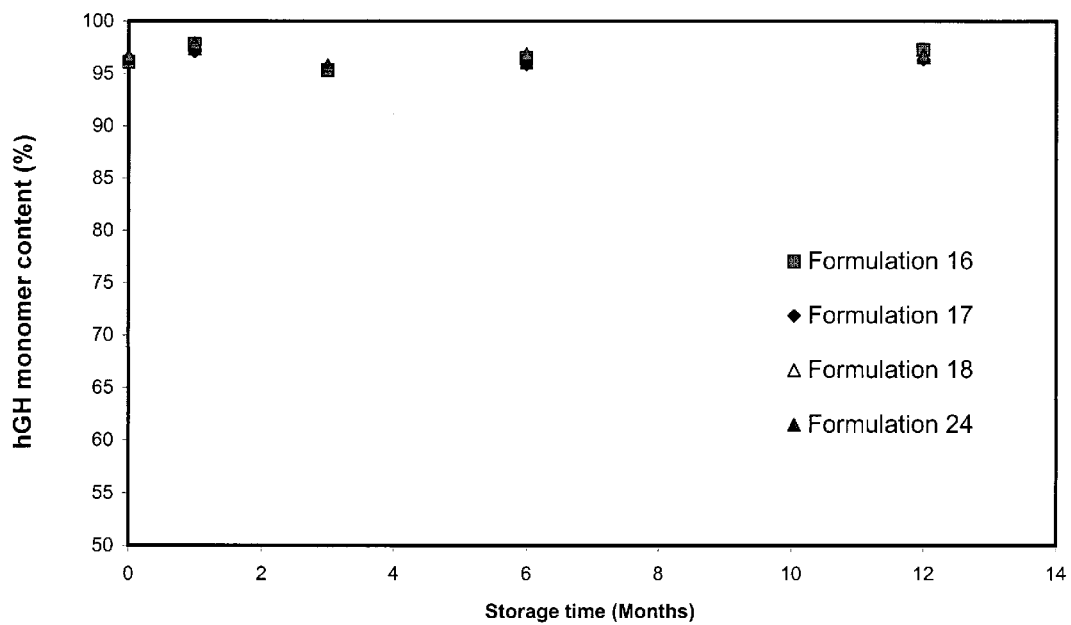
FIG. 16 illustrates the stability of hGH in the various depot formulations, including those of the present invention, as a function of time at 5° C.

Depot gel hGH formulations were stored at 5° C. At predetermined time points, the depot gel hGH formulation (0.3 ml) was treated with a cooled organic solvent (a 50/50 mixture of methylene chloride/acetone, 5° C., 3×3 ml) to extract the polymer and solvents from the depot formulation. The resulting residual hGH was dissolved in a PBS buffer (2 ml, pH 7.4) and the purity of the hGH was analyzed by size exclusion chromatography (SEC). FIG. 16 illustrates the stability of hGH in the various depot gel hGH formulations, including those of the present invention, as a function of time at 5° C. The stability of hGH in the depot formulations comprising benzyl alcohol (e.g., formulations 18 and 25) is comparable to the control formulations without benzyl alcohol (e.g., formulations 16 and 17). Thus, the depot formulations of the present invention reduce the injection force significantly without compromising the stability of the beneficial agent, e.g., hGH.

Example 16

Parameters Affecting the Injection Force

The following parameters affect the injection force for a given formulation at a preset temperature: the radius of syringe (r); inner radius of needle (R); needle length (L); and injection speed (Q). The effect of these four parameters on the injection force was determined using a fractional factorial design approach (8 trials) with one near center point for confirmation. The details of the design are summarized in Table 6 (trials 1-9). The injection force was tested using the following formulation (n=3): the vehicle containing PLGA RG502/BB/BA (40/45/15 wt %), loaded with lysozyme particles (10 wt % 30 µm). The correlation between the injection force and testing parameters was established using JMP software (which is very similar to the Power Law prediction) as follows:

$$F = 0.028 \cdot \frac{r^{2.475} \cdot L^{0.770} \cdot Q^{0.716}}{R^{2.630}}$$

TABLE 6

| Trial | Needle ID[a] (mm) | Needle length[b] (mm) | Syringe ID[c] (mm) | Injection speed (mL/min) | Injection Force (N) Avg | SD |
|---|---|---|---|---|---|---|
| 1 | 0.191 | 12.7 | 2.3 | 0.05 | 14.6 | 0.8 |
| 2 | 0.292 | 50.8 | 3.25 | 0.5 | 172.2 | 5.3 |
| 3 | 0.292 | 12.7 | 0.05 | 0.05 | 8.6 | 0.2 |
| 4 | 0.191 | 12.7 | 3.25 | 0.5 | 176.0 | 2.6 |
| 5 | 0.292 | 50.8 | 2.3 | 0.05 | 13.4 | 0.3 |
| 6 | 0.292 | 12.7 | 2.3 | 0.5 | 30.0 | 2.5 |
| 7 | 0.191 | 50.8 | 3.25 | 0.05 | 127.0 | 2.3 |
| 8 | 0.191 | 50.8 | 2.3 | 0.5 | 161.4 | 4.5 |
| 9 | 0.241 | 25.4 | 2.3 | 0.25 | 48.8 | 0.5 |

[a]Needles having following gauges were used: 24G (ID = 0.292 mm), 25G (ID = 0.241 mm) and 27G (ID = 0.191 mm);
[b]Needle having following lengths were used: 0.5 inch (12.7 mm), 1 inch (25.4 mm), 2 inches (50.8 mm);
[c]Two different syringes (Hamilton): 250 µL (ID = 2.30 mm); 500 µL (ID = 3.25 mm).

Example 17

Figure 17:
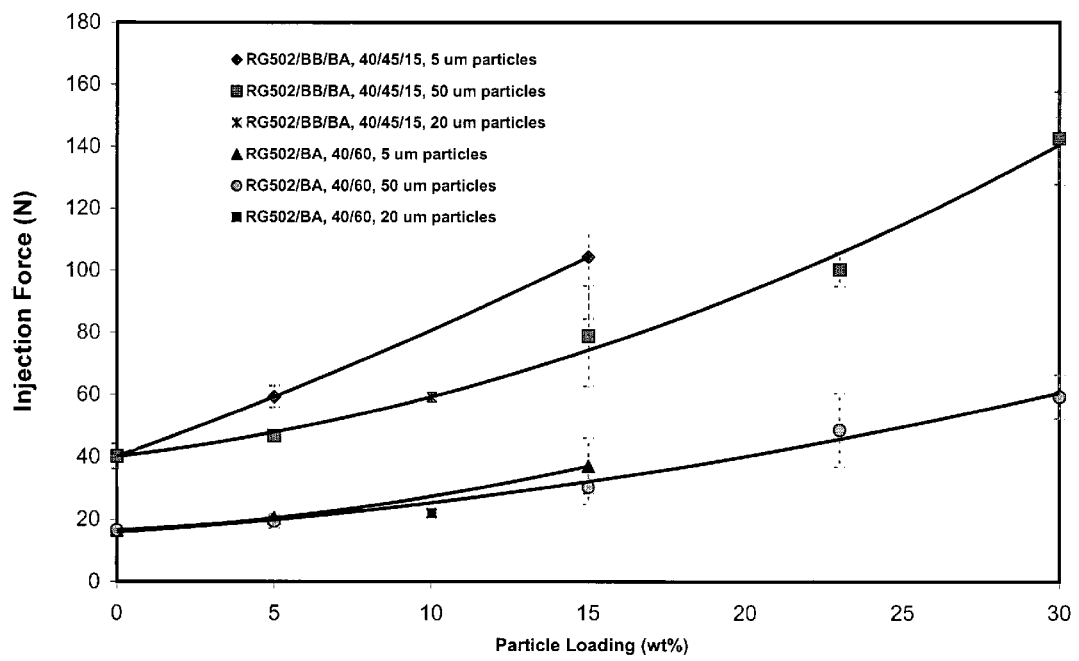
FIG. 17 illustrates the injection force of various depot formulations, including those of the present invention, as a function of the loading levels and the particle sizes of beneficial agent.

Effect of Drug Particle Size and Loading on the Injection Force of Depot Formulations Particle size and amount of loading of the beneficial agent, i.e., drug, are additional factors potentially affecting the injection force of the depot formulation. Depot gel lysozyme formulations were used to determine the effect of drug particle size and loading on the injection force of the depot formulations. Various depot gel lysozyme formulations of the present invention containing differing amounts (5-30% loading) and particle sizes (5-50 µm) of lysozyme were tested for injection force using 27-gauge, 2" needles. The injection speed was set at 50 µl/min. The formulations tested are summarized in Table 7. As illustrated in FIG. 17, the injection force of the depot formulations increases with the increase of drug particle loading. With 10 wt % particle loading, the injection forces increase about 50% compared to the corresponding gel formulation, regardless of the composition of the gel formulation. The injection force appears to be proportional to the amount of benzyl alcohol in the gel formulation, further indicating that benzyl alcohol significantly reduces the injection force of the depot gel formulations of the invention.

TABLE 7

| Formulation | PLGA RG 502 (wt %) | Benzyl Benzoate (BB, wt %) | Benzyl Alcohol (BA, wt %) | Particle loading (wt %) | Particle size (µm) |
|---|---|---|---|---|---|
| 25 | 38.0 | 42.8 | 14.2 | 5 | 5 |
| 26 | 34.0 | 38.3 | 12.8 | 15 | 5 |
| 27 | 38.0 | 42.8 | 14.2 | 5 | 50 |
| 28 | 34.0 | 38.3 | 12.8 | 15 | 50 |
| 29 | 36.0 | 40.5 | 13.5 | 10 | 20 |
| 30 | 38.0 | — | 57.0 | 5 | 5 |
| 31 | 34.0 | — | 51.0 | 15 | 5 |
| 32 | 38.0 | — | 57.0 | 5 | 50 |
| 33 | 34.0 | — | 51.0 | 15 | 50 |
| 34 | 36.0 | — | 54.0 | 10 | 20 |
| 35 | 30.8 | 34.7 | 11.6 | 23 | 50 |
| 36 | 28.0 | 31.5 | 10.5 | 30 | 50 |
| 37 | 30.8 | — | 46.2 | 23 | 50 |
| 38 | 28.0 | — | 42.0 | 30 | 50 |
| 39 | 40.0 | 45.0 | 15.0 | 0 | — |
| 40 | 40.0 | — | 60.0 | 0 | — |

Example 18

PDGF Preformulation Preparation

Various Platelet Derived Growth Factor (PDGF) preformulations were prepared as follows:

Dialysis

The following buffers were prepared for the dialysis:
The histidine buffer (10 mM, pH 6, 2 L) was prepared as follows. L-histidine (3.10 g) was weighed in a volumetric flask (2 L). Milli-Q water (1800 ml) was added to the flask and the mixture was stirred until the solid dissolved. HCl (0.1N, 8 ml) was added, the pH was checked and adjusted to 6. The solution was diluted with milli-Q water to a volume of 2 L. The succinate buffer (10 mM, pH 6, 2 L) was prepared as follows. Succinic acid (5.91 g) was weighed in a volumetric flask (250 ml) and milli-Q water (250 ml) was added to obtain succinic acid solution (0.2 M). NaOH solution (4 g, 50% w/w) was measured in a volumetric flask (250 ml) and diluted with milli-Q water to obtain NaOH solution (0.2 M). The succinic acid solution (0.2 M, 100 ml) was mixed with the NaOH solution (0.2 M, 165 ml) and milli-Q water (1600 ml) in a volumetric flask (2 L) the pH was checked and adjusted to 6. The solution was diluted with milli-Q water to a volume of 2 L.

The PDGF-BB bulk solution, i.e., aqueous solution of PDGF in acetate buffer, was thawed to room temperature. Various aliquots of the PDGF-BB solution were diluted appropriately for a UV absorbance measurement, using a 1 cm path length cuvette from 400 to 250 nm. The absorbance was recorded at 280 nm and corrected for light scattering in the 400 to 330 nm range using a log(Absorbance) vs. log (wavelength) extrapolation. The concentration of PDGF-BB was determined using an extinction coefficient of 0.574 ml/mg*cm. The PDGF-BB solution was concentrated using a Millipore Tangential Flow Filtration System (having a reservoir (100 ml) and a Pellicon XL PLCCC 5000 MWCO regenerated cellulose membrane), and the protein was divided into two parts. One half of the protein was diafiltrated against the histidine buffer (10 mM, pH 6); and the second half of the protein was diafiltered against the succinate buffer (10 mM, pH 6), according to manufacturer's instructions. After diafiltration, an aliquot from each part was appropriately diluted for an absorbance measurement as described above, and analyzed by reverse phase and size exclusion high pressure liquid chromatography (HPLC). The protein solution was removed from the TFF system according to Millipore TFF instructions.

PDGF-BB Preformulation

Various preformulations of PDGF-BB were prepared by adding different excipients, e.g., sucrose, tween 20, Zn acetate or combinations thereof, into the above diafiltrated PDGF-BB solution; the solution was buffered either with histidine or succinate to obtain the final PDGF-BB concentration in the solution of approximately 5 mg/ml (as tabulated in Tables 8 and 9). Those solutions were lyophilized under the conditions described below to achieve the dry PDGF-BB formulations.

Lyophilization

The lyophilization freezing cycle was started with an equilibration of shelf temperature at 4° C. at 2.5° C./min and held at this temperature for 30 minutes. The temperature was then brought down to −50° C. at 2.5° C./min and held for 3 hours. For the primary drying cycle, vacuum was applied and the shelf temperature was increased as follows: (i) −20° C. at 0.14° C./min for 24 hours; (ii) −15° C. at 0.14° C./min for 24 hours; and (iii) 0° C. at 0.14° C./min for 12 hours. For the secondary drying cycle, the shelf temperature was increased as follows: (i) 20° C. at 0.14° C./min for 12 hours; and (ii) 30° C. at 0.14° C./min for 4 hours. After drying, shelf temperature was decreased to 0° C. or 4° C. and held at that temperature until removal from the instrument. The vials were capped using shelf stoppering, the run was stopped, and the vials were removed.

Example 19

Preliminary Stability of PDGF Preformulations in the Gel Vehicle

All lyophilized protein formulations as listed in Tables 8 and 9, were mixed into a gel vehicle with the composition of PLGA RG502/Benzyl Benzoate (BB)/benzyl alcohol (BA) of 40/45/15 with the loading of the protein formulation about 10 wt %. After being stored at 5° C. for 1 day, the mixtures were extracted with an organic solvent mixture of methylene chloride and acetone (ratio of 50/50) as described in the example 15 above. The purity of the PDGF-BB was analyzed by both reverse phase HPLC (rpHPLC) and size exclusion chromatography (SEC). The stability data of the PDGF-BB formulation after mixing with the gel vehicle are summarized in Tables 8 and 9. In general, no distinguishable degradation of the PDGF-BB was found in the PDGF-BB formulation incorporated with the excipients as described in the Example 18 and mixed with the gel vehicle of the present invention.

TABLE 8

| Formulation | SA-1 | SA-2 | SA-3 | SA-4 | SA-5 | Bulk PDGF |
|---|---|---|---|---|---|---|
| PDGF (mg) | 1 | 1 | 1 | 1 | 1 | |
| Sucrose (mg) | 1 | 1 | 0 | 0 | 0 | |
| Tween 20 (mg) | 0 | 0.2 | 0.2 | 0 | 0 | |
| Succinate (mg) | 0.24 | 0.24 | 0.24 | 0.24 | 0.24 | |
| Zn acetate (mg) | 0 | 0 | 0 | 0 | 0.02 | |
| Gel vehicle (mg)[a] | 20.16 | 21.96 | 12.96 | 11.16 | 11.34 | |
| % PDGF monomer by SEC | 98.90 | 98.82 | 98.02 | 98.51 | 98.59 | 99.27 |
| % PDGF dimmer by SEC | 1.10 | 1.18 | 1.98 | 1.49 | 1.41 | 0.73 |
| % peak at RRT = 0.93 by rp-HPLC | 11.5 | 11.1 | 10.7 | 12.7 | 11.0 | 11.1 |
| % peak at RRT = 1.00 by rp-HPLC | 87.3 | 87.6 | 87.6 | 86.2 | 87.8 | 87.7 |
| % peak at RRT = 1.10 by rp-HPLC | 1.1 | 1.2 | 1.1 | 1.1 | 1.1 | 1.2 |
| % other peaks by rp-HPLC | 0.0 | 0.1 | 0.6 | 0.0 | 0.0 | 0.0 |

[a] = PLGA RG502/BB/BA - 40/45/15

TABLE 9

| Formulation | HA-1 | HA-2 | HA-3 | HA-4 | HA-5 | Bulk PDGF |
|---|---|---|---|---|---|---|
| PDGF (mg) | 1 | 1 | 1 | 1 | 1 | |
| Sucrose (mg) | 1 | 1 | 0 | 0 | 0 | |
| Tween 20 (mg) | 0 | 0.2 | 0.2 | 0 | 0 | |
| Histidine (mg) | 0.31 | 0.31 | 0.31 | 0.31 | 0.31 | |
| Zn acetate (mg) | 0 | 0 | 0 | 0 | 0.02 | |
| Gel vehicle (mg)[a] | 20.79 | 22.59 | 13.59 | 11.79 | 11.97 | |
| % PDGF monomer by SEC | 99.15 | 99.15 | 99.07 | 99.01 | 99.04 | 99.27 |
| % PDGF dimer by SEC | 0.85 | 0.85 | 0.93 | 0.99 | 0.96 | 0.73 |
| % peak at RRT = 0.93 by rp-HPLC | 11.3 | 11.0 | 10.9 | 10.8 | 10.9 | 11.1 |
| % peak at RRT = 1.00 by rp-HPLC | 87.6 | 87.8 | 87.7 | 88.0 | 88.0 | 87.7 |
| % peak at RRT = 1.10 by rp-HPLC | 1.1 | 1.1 | 1.2 | 1.2 | 1.1 | 1.2 |
| % other peaks by rp-HPLC | 0.0 | 0.0 | 0.2 | 0.0 | 0.0 | 0.0 |

[a] = PLGA RG502/BB/BA - 40/45/15

Example 20

Preparation of PDGF Particles

PDGF-BB formulations with sucrose in histidine buffer and without sucrose in succinate buffer were prepared as a similar way to the Example 18 above (Table 10): Thaw PDGF-BB bulk solution. Combine the solution and measure volume in a graduated cylinder. Take an aliquot and dilute appropriately for a UV absorbance measurement. Record the absorbance in a 1 cm path length cuvette from 400 to 250 nm. Record the absorbance at 280 nm and correct for light scattering in the 400 to 330 nm range using a log(Absorbance) vs. log(wavelength) extrapolation. Determine the concentration of PDGF-BB using an extinction coefficient of 0.574 ml/mg× cm. Using a Millipore Tangential Flow Filtration System with 100 ml reservoir and a Pellicon XL PLCCC 5000 MWCO regenerated cellulose membrane, concentrate if necessary, and diafilter half of the protein against 10 mM histidine pH 6 and concentrate, if necessary, and diafilter the other half against 10 mM succinate pH 6, according to TFF instructions. After diafiltration, remove an aliquot from each and dilute appropriately for a UV absorbance measurement and analyze by reverse phase and size exclusion HPLC. Remove all of the protein solution from the TFF system according to Millipore TFF instructions. For PDGF-BB in 10 mM histidine add sucrose to give a 1:1 final ratio with the protein (PDGF-BB at a final concentration of approximately 5 mg/ml). For the PDGF-BB in 10 mM succinate pH 6 dilute with 10 mM succinate to give a final protein concentration of approximately 5 mg/ml. Aliquot formulations were placed into glass lyophilization vials and were lyophilized under the conditions described in the Example 18 to achieve the lyophilized dry PDGF-BB formulations. Lyophilized PDGF formulations were ground in an agate mortar and pestle. The grounded particles were sieved through a US #230 Mesh Screen (63 μm) and were collected on a US #500 Mesh Screen (25 μm).

TABLE 10

| Formulation | PDGF-BB (wt %) | Succinate (wt %) | Histidine (wt %) | Sucrose (wt %) |
|---|---|---|---|---|
| 41 | 81 | 19 | — | — |
| 42 | 43 | — | 14 | 43 |

Example 21

Preparation of PDGF Depot Formulations

The PDGF depot formulations were prepared in two steps. The first step was to make the gel formulations using the procedure as described below. Appropriate amounts of pre-irradiated PLGA RG 502 and solvent were dispensed into the Keyence hybrid mixer bowl (made from high density polyethylene (HDPE)). The mixing bowl was tightly sealed, placed into the hybrid mixer (Model HM-501, Keyence Corp., Japan) and mixed (5-10 minutes) at the mixing speed (revolution 2000 rpm, rotation 800 rpm).

Mixing of particles in the gel was performed at room temperature in a glass syringe (10 ml or 25 ml). The PDGF particles and gel were first weighed and transferred into the syringe. Then, the PDGF particles and gel mixture were thoroughly blended by conventional mixing using a Caframo mechanical stirrer with an attached square-tip metal spatula. Resulting formulations are tabulated in Table 11.

TABLE 11

| Formulation | Polymer (%) (PLGA RG-502, MW = 16,000) | Benzyl Benzoate (%) | Benzyl Alcohol (%) |
|---|---|---|---|
| 43[a] | 31.5 | 43.9 | 14.6 |
| 44[b] | 31.5 | 43.9 | 14.6 |
| 45[a] | 31.5 | 29.3 | 29.2 |
| 46[b] | 31.5 | 29.3 | 29.2 |

[a] = 10% formulation 41;
[b] = 10% formulation 42.

Example 22

Stability of PDGF in the Depot Formulations

Figure 18:
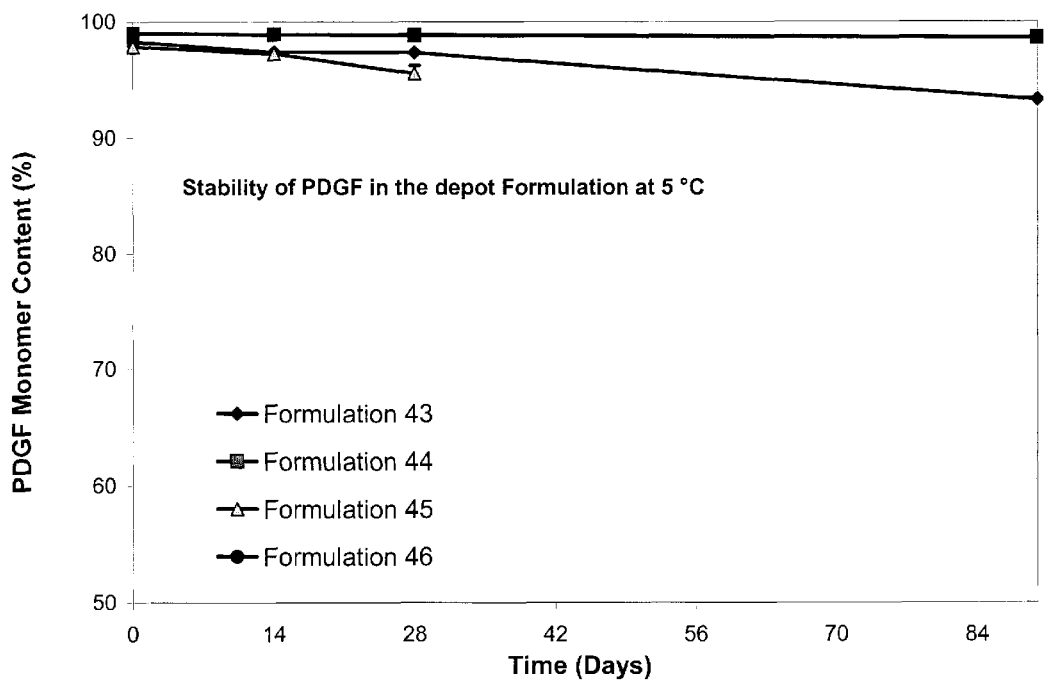
FIG. 18 illustrates the stability of PDGF in the various depot formulations, including those of the present invention, as a function of time at 5° C.
Figure 19:
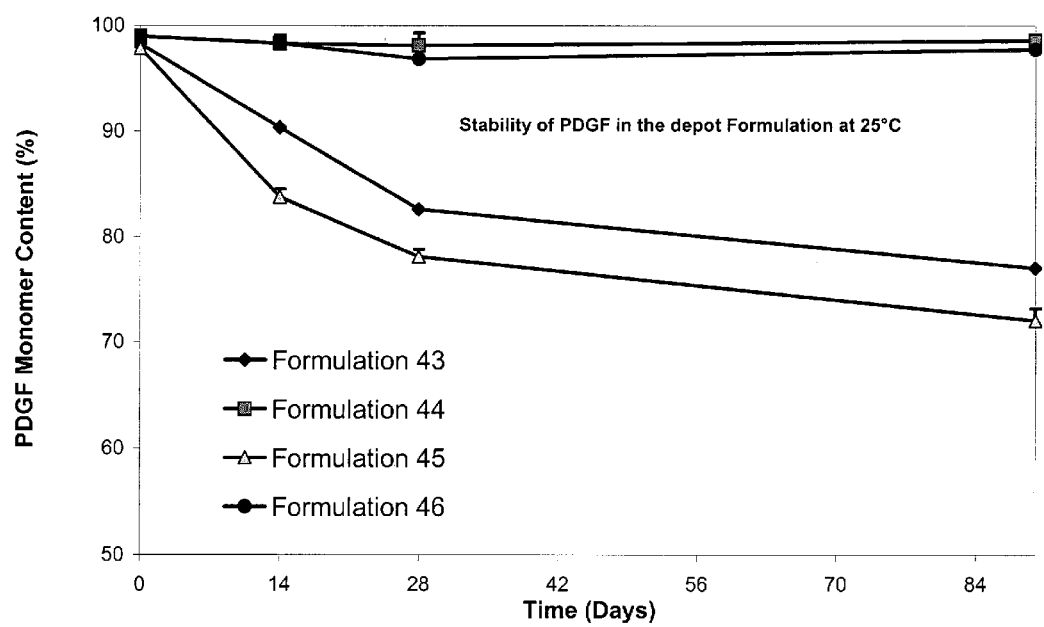
FIG. 19 illustrates the stability of PDGF in the various depot formulations, including those of the present invention, as a function of time at 25° C.
Figure 20:
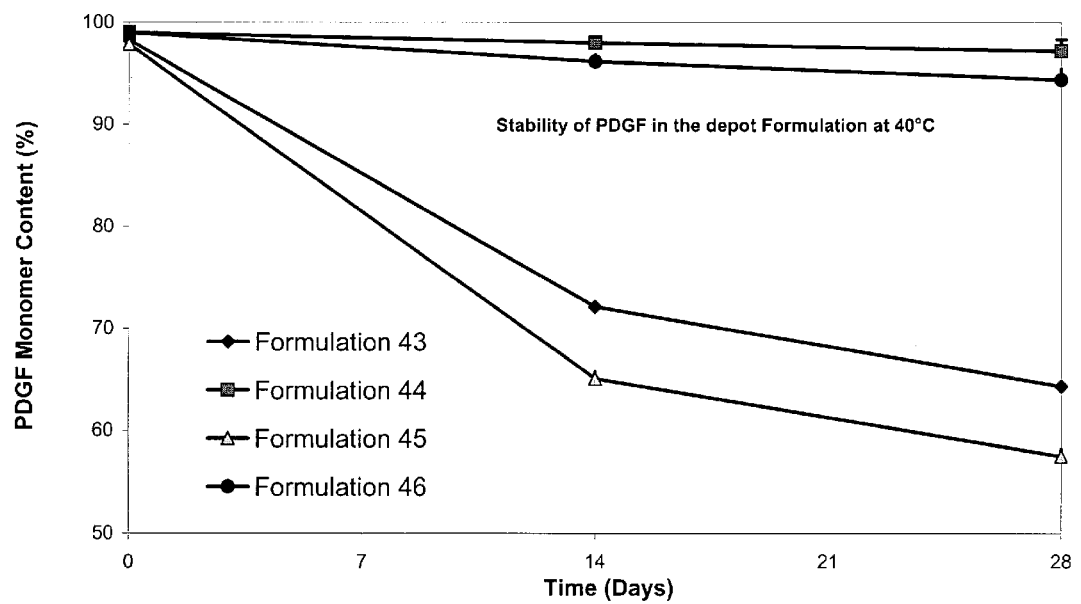
FIG. 20 illustrates the stability of PDGF in the various depot formulations, including those of the present invention, as a function of time at 40° C.

Depot gel PDGF formulations were stored for different periods of time at 5, 25 and 40° C., respectively. At predetermined time points, the depot gel PDGF-BB formulation (0.3 ml) was treated with a cooled organic solvent (a 50/50 mixture of methylene chloride/acetone, at 5° C., 3×3.0 ml). The resulting residual PDGF-BB was dissolved in a PBS buffer (ca. 2 ml, pH 7.4) and the purity of the PDGF was analyzed by both reverse phase HPLC (rpHPLC) and size exclusion chromatography (SEC) HPLC. FIGS. 18-20 illustrate the stability of PDGF (% monomer by SEC) in the various depot formulations, including those of the present invention, as a function of time at 5° C. (FIG. 18), 25° C. (FIG. 19) and 40° C. (FIG. 20), respectively. Table 12 summarizes the chemical stability of PDGF tested by rpHPLC in the various depot formulations, including those of the present invention, as a function of time at 5° C., 25° C. and 40° C., respectively. As illustrated in FIGS. 18-20 and Table 12, depot gel PDGF formulations containing sucrose demonstrated surprisingly good stability with minimal lose of monomer content and chemical degradation, as compared to the depot gel PDGF formulations without sucrose, at all temperatures measured. Sucrose has a significant stabilizing effect on the various depot formulations of the present invention.

TABLE 12

| | | | RP-HPLC (% Peak Area) | | | |
|---|---|---|---|---|---|---|
| Formulation | Temp. | Time (day) | Peak at (RRT = 0.93) | Peak at (RRT = 1.00) | Peak at (RRT = 1.09) | Other Peak(s) |
| Bulk PDGF | | 0 | 11.1 | 87.7 | 1.2 | 0 |
| 43 | | 0 | 13.03 ± 0.12 | 85.04 ± 0.43 | 1.2 ± 0.35 | 0.72 ± 0.09 |
| | 5° C. | 14 | 12.77 ± 0.28 | 85.94 ± 0.17 | 1.06 ± 0.03 | 0.23 ± 0.19 |
| | 5° C. | 28 | 12.17 ± 0.32 | 86.03 ± 0.77 | 1.11 ± 0.34 | 0.69 ± 0.08 |
| | 5° C. | 90 | 12.14 ± 0.35 | 86.14 ± 0.42 | 0.78 ± 0.01 | 0.94 ± 0.08 |
| | 25° C. | 14 | 9.57 ± 0.14 | 89.52 ± 0.18 | (shoulder) | 0.91 ± 0.03 |
| | 25° C. | 28 | 8.24 ± 0.12 | 90.98 ± 0.09 | (shoulder) | 0.78 ± 0.04 |
| | 25° C. | 90 | 8.96 ± 0.21 | 90.16 ± 0.23 | (N/A) | 0.88 ± 0.01 |
| | 40° C. | 14 | 7.22 ± 0.06 | 91.96 ± 0.09 | (shoulder) | 0.83 ± 0.02 |
| | 40° C. | 28 | 5.54 ± 0.13 | 93.80 ± 0.09 | (shoulder) | 0.66 ± 0.09 |
| 44 | | 0 | 13.25 ± 0.16 | 84.97 ± 0.34 | 1.5 ± 0.36 | 0.28 ± 0.86 |
| | 5° C. | 14 | 13.07 ± 0.04 | 85.32 ± 0.34 | 1.43 ± 0.36 | 0.18 ± 0.03 |
| | 5° C. | 28 | 12.93 ± 0.08 | 85.62 ± 0.43 | 1.27 ± 0.37 | 0.18 ± 0.06 |
| | 5° C. | 90 | 14.07 ± 0.25 | 83.87 ± 0.41 | 1.39 ± 0.44 | 0.67 ± 0.28 |
| | 25° C. | 14 | 12.19 ± 0.10 | 86.28 ± 0.52 | 1.25 ± 0.33 | 0.28 ± 0.13 |
| | 25° C. | 28 | 11.79 ± 0.27 | 86.82 ± 0.09 | 1.30 ± 0.35 | 0.10 ± 0.02 |
| | 25° C. | 90 | 14.57 ± 0.11 | 83.84 ± 0.57 | 1.43 ± 0.46 | 0.17 ± 0.00 |
| | 40° C. | 14 | 12.93 ± 0.08 | 85.65 ± 0.26 | 1.26 ± 0.39 | 0.16 ± 0.07 |
| | 40° C. | 28 | 13.09 ± 0.24 | 85.18 ± 0.17 | 1.59 ± 0.43 | 0.15 ± 0.04 |

TABLE 12-continued

| Formulation | Temp. | Time (day) | RP-HPLC (% Peak Area) | | | |
|---|---|---|---|---|---|---|
| | | | Peak at (RRT = 0.93) | Peak at (RRT = 1.00) | Peak at (RRT = 1.09) | Other Peak(s) |
| 45 | | 0 | 12.39 ± 0.28 | 85.91 ± 0.26 | 0.96 ± 0.02 | 0.73 ± 0.04 |
| | 5° C. | 14 | 12.21 ± 0.29 | 86.05 ± 0.34 | 1.10 ± 0.32 | 0.64 ± 0.36 |
| | 5° C. | 28 | 11.38 ± 0.18 | 87.11 ± 0.70 | 0.81 ± 0.04 | 0.97 ± 0.08 |
| | 25° C. | 14 | 8.50 ± 0.19 | 90.40 ± 0.27 | (shoulder) | 1.10 ± 0.08 |
| | 25° C. | 28 | 7.73 ± 0.19 | 91.25 ± 0.18 | (shoulder) | 1.02 ± 0.04 |
| | 25° C. | 90 | 7.48 ± 0.64 | 91.67 ± 0.66 | (N/A) | 0.86 ± 0.01 |
| | 40° C. | 14 | (shoulder) | 99.17 ± 0.00 | (shoulder) | 0.83 ± 0.04 |
| | 40° C. | 28 | (shoulder) | 99.56 ± 0.00 | (shoulder) | 0.44 ± 0.03 |
| 46 | | 0 | 12.71 ± 0.14 | 85.90 ± 0.26 | 1.1 ± 0.01 | 0.3 ± 0.03 |
| | 5° C. | 14 | 13.04 ± 0.25 | 85.10 ± 0.60 | 1.45 ± 0.37 | 0.41 ± 0.13 |
| | 5° C. | 28 | 12.67 ± 0.20 | 86.05 ± 0.17 | 1.04 ± 0.02 | 0.24 ± 0.05 |
| | 5° C. | 90 | 14.65 ± 0.08 | 83.65 ± 0.07 | 1.04 ± 0.01 | 0.66 ± 0.13 |
| | 25° C. | 14 | 12.94 ± 0.06 | 85.27 ± 0.43 | 1.50 ± 0.33 | 0.29 ± 0.10 |
| | 25° C. | 28 | 12.64 ± 0.19 | 85.55 ± 0.34 | 1.51 ± 0.41 | 0.30 ± 0.09 |
| | 25° C. | 90 | 14.11 ± 0.15 | 84.68 ± 0.10 | 1.01 ± 0.01 | 0.21 ± 0.04 |
| | 40° C. | 14 | 12.10 ± 0.18 | 85.76 ± 0.34 | 1.26 ± 0.39 | 0.87 ± 0.46 |
| | 40° C. | 28 | 11.12 ± 0.22 | 88.05 ± 0.88 | (shoulder) | 0.19 ± 0.03 |

Example 23

In Vitro Release of PDGF from the Depot Formulations

Figure 21:
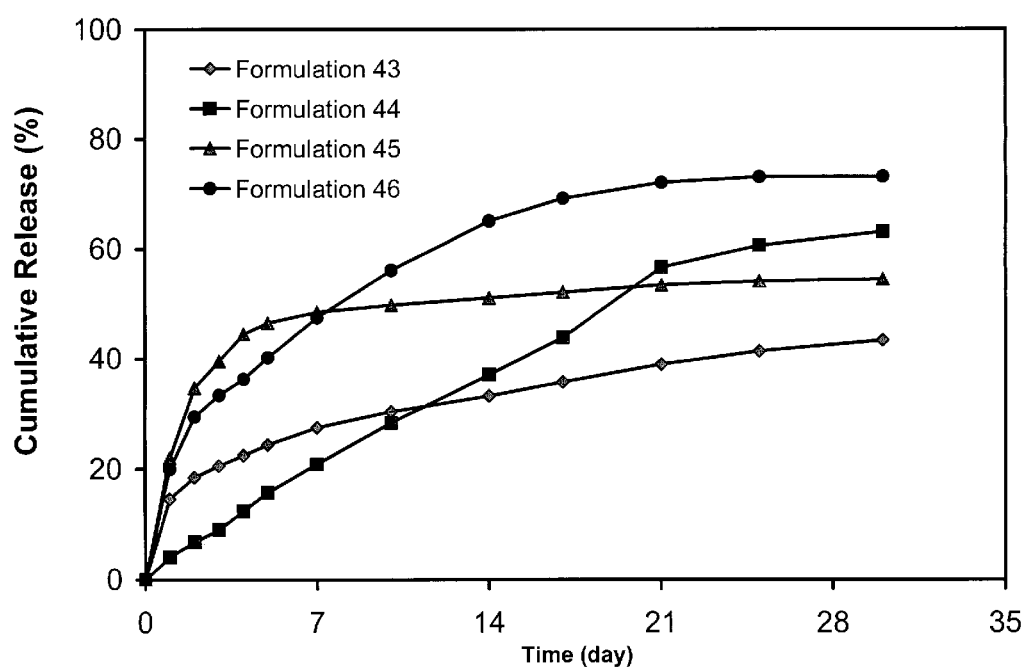
FIG. 21 is a graph illustrating the in vitro release of PDGF obtained from various depot compositions, including those of the present invention (Formulations 43-46).

The in vitro release of PDGF from the depot gel PDGF formulation of the present invention was performed as follows. The depot gel PDGF formulation (80-120 mg) was loaded into a tea bag and placed in a 20 mL scintillation vial and the release medium (5 mL, phosphate buffer saline (PBS)+0.1% Tween 20, pH 7.4) was added to the vial. The vial was incubated in a 37° C. water bath with gentle agitation. The medium was replaced daily for the first 5 days, then twice a week thereafter until the end of the release duration. The amount of PDGF released from the depot was measured by size exclusion chromatography (SEC) HPLC. As illustrated in FIG. 21, sustained release of PDGF from the depot formulations of the present invention was obtained for over a month.

We claim:

1. An injectable depot composition comprising:
   (a) a bioerodible, biocompatible polymer;
   (b) a solvent selected from the group consisting of aromatic alcohols, esters of aromatic acids, aromatic ketones, and mixtures thereof, said solvent having a miscibility in water of less than or equal to 7% at 25° C., and present in an amount effective to plasticize the polymer and form a gel therewith;
   (c) a thixotropic amount of a thixotropic agent mixed with the polymer effective to form a thixotropic composition, the thixotropic agent comprising a lower alkanol and said amount being between 0.01 weight percent and 15 weight percent of the combined weight of the solvent and the thixotropic agent; and
   (d) a beneficial agent;
   wherein the injectable depot composition does not comprise an emulsion.

2. The injectable depot composition of claim 1, wherein the solvent is a mixture of the aromatic alcohol and the ester of the aromatic acid.

3. The injectable depot composition of claim 2, wherein the aromatic alcohol is benzyl alcohol and the ester of the aromatic acid is a lower alkyl ester or an aralkyl ester of benzoic acid.

4. The injectable depot composition of claim 3, wherein the ester of the aromatic acid is benzyl benzoate and the lower alkyl ester of the aromatic acid is ethyl benzoate.

5. An injectable depot composition comprising:
   (a) approximately 5 wt. % to approximately 90 wt. % of a biodegradable, biocompatible lactic acid-based polymer having an average molecular weight in the range of approximately 1,000 to approximately 120,000;
   (b) a solvent selected from the group consisting of an aromatic alcohol, an ester of an aromatic acid, and mixtures thereof, said solvent having a miscibility in water of less than or equal to 7% at 25° C., and present in an amount effective to plasticize the polymer and form a gel therewith, wherein the aromatic alcohol has the structural formula (I)

$$Ar-(L)_n-OH \qquad (I)$$

in which Ar is a substituted or unsubstituted aryl or heteroaryl group, n is zero or 1, and L is a linking moiety;
   (c) a thixotropic amount of a thixotropic agent mixed with the polymer effective to form a thixotropic composition, the thixotropic agent comprising a lower alkanol and said amount being between 0.01 Weight percent and 15 weight percent of the combined weight of the solvent and the thixotropic agent; and
   (d) a beneficial agent;
   wherein the injectable depot composition does not comprise an emulsion.

6. The injectable depot composition of claim 5, wherein the solvent is a mixture of the aromatic alcohol and the ester of the aromatic acid.

7. The injectable depot composition of claim 6, wherein the aromatic alcohol is benzyl alcohol and the ester of the aromatic acid is a lower alkyl ester or an aralkyl ester of benzoic acid.

8. The injectable depot composition of claim 7, wherein the ester of the aromatic acid is benzyl benzoate and the lower alkyl ester of the aromatic acid is ethyl benzoate.

9. The injectable depot composition of claim 8, wherein the thixotropic agent is ethanol.

10. The injectable depot composition of claim 6, wherein a ratio of the aromatic alcohol to the ester of the aromatic acid is in the range of about 1% to about 99% by weight.

11. The injectable depot composition of claim 10, wherein the ratio of the aromatic alcohol to the ester of the aromatic acid is in the range of about 20% to about 80% by weight.

12. The injectable depot composition of claim 5, wherein the beneficial agent is selected from a drug, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents, antiproliferative agents, antimitotic agents, angiogenic agents, anticoagulants, fibrinolytic agents, growth factors, antibodies, and ocular drugs.

13. The injectable depot composition of claim 12, wherein the beneficial agent is a growth factor.

14. The injectable depot composition of claim 12, wherein the beneficial agent is present in an amount of from 0.1 to 50% by weight of the combined amounts of the polymer, the solvent and the beneficial agent.

15. The injectable depot composition of claim 12, wherein the beneficial agent is in a form of particles dispersed or dissolved in the gel.

16. The injectable depot composition of claim 15, wherein the beneficial agent is in the form of the particles having an average particle size of from 0.1 to 250 microns.

17. The injectable depot composition of claim 15, wherein the beneficial agent is in the form of the particles, wherein the particles further comprise a component selected from the group consisting of a stabilizing agent, bulking agent, chelating agent, and buffering agent.

18. The injectable depot composition of claim 5, wherein the beneficial agent is a growth hormone.

19. An injectable depot composition comprising:
(a) approximately 5 wt. % to approximately 90 wt. % of a poly(lactide-co-glycolide) (PLGA) copolymer having an average molecular weight in the range of approximately 1,000 to approximately 120,000;
(b) approximately 5 wt. % to approximately 90 wt. % of a solvent selected from the group consisting of an aromatic alcohol, an ester of an aromatic acid, and mixtures thereof, said solvent having a miscibility in water of less than or equal to 7% at 25° C., and present in an amount effective to plasticize the polymer and form a gel therewith;
(c) a thixotropic amount of a thixotropic agent mixed with the polymer effective to form a thixotropic composition, wherein the thixotropic agent is ethanol and an amount of ethanol is greater than or equal to 0.01 weight percent and less than or equal to 15 weight percent of the combined weight of the solvent and the thixotropic agent; and
(d) a beneficial agent;
wherein the injectable depot composition does not comprise an emulsion.

20. The injectable depot composition of claim 19, wherein the aromatic alcohol is benzyl alcohol and the ester of the aromatic acid is benzyl benzoate.

21. A method of administering a beneficial agent to a subject comprising:
(1) administering an injectable depot composition to the subject at a site within the subject, the composition comprising:
(a) a bioerodible, biocompatible polymer;
(b) a solvent selected from the group consisting of aromatic alcohols, esters of aromatic acids, aromatic ketones, and mixtures thereof, said solvent having a miscibility in water of less than or equal to 7% at 25° C., and present in an amount effective to plasticize the polymer and form a gel therewith;
(c) a thixotropic amount of a thixotropic agent mixed with the polymer effective to form a thixotropic composition, the thixotropic agent comprising a lower alkanol and said amount being less than 15 weight percent of the combined weight of the solvent and the thixotropic agent; and
(d) a beneficial agent; and
(2) forming an implant at the site wherein the implant provides sustained release of the beneficial agent at the site;
wherein the injectable depot composition does not comprise an emulsion.

22. The method of claim 21, wherein the solvent is a mixture of the aromatic alcohol and the ester of the aromatic acid.

23. The method of claim 22, wherein the aromatic alcohol is benzyl alcohol and the ester of the aromatic acid is a lower alkyl ester or an aralkyl ester of benzoic acid.

24. The method of claim 23, wherein the ester of the aromatic acid is benzyl benzoate and the lower alkyl ester of the aromatic acid is ethyl benzoate.

25. A method of administering a beneficial agent to a subject to provide sustained release of the beneficial agent to the subject, the method comprising:
(1) administering an injectable depot composition to the subject at a site within the subject, the composition comprising:
(a) approximately 5 wt. % to approximately 90 wt. % of a biodegradable, biocompatible lactic acid-based polymer having an average molecular weight in the range of approximately 1,000 to approximately 120,000;
(b) a solvent selected from the group consisting of an aromatic alcohol, an ester of an aromatic acid, and mixtures thereof, said solvent having a miscibility in water of less than or equal to 7% at 25° C., and present in an amount effective to plasticize the polymer and form a gel therewith, wherein the aromatic alcohol has the structural formula (I)

Ar-(L)$_n$-OH         (I)

in which Ar is a substituted or unsubstituted aryl or heteroaryl group, n is zero or 1, and L is a linking moiety;
(c) a thixotropic amount of a thixotropic agent mixed with the polymer effective to form a thixotropic composition, the thixotropic agent comprising a lower alkanol and said amount being less than 15 weight percent of the combined weight of the solvent and the thixotropic agent; and
(d) a beneficial agent; and
(2) forming an implant at the site wherein the implant provides sustained release of the beneficial agent at the site;
wherein the injectable depot composition does not comprise an emulsion.

26. The method of claim 25, wherein the solvent is a mixture of the aromatic alcohol and the ester of the aromatic acid.

27. The method of claim 26, wherein the aromatic alcohol is benzyl alcohol and the ester of the aromatic acid is a lower alkyl ester or an aralkyl ester of benzoic acid.

28. The method of claim 27, wherein the ester of the aromatic acid is benzyl benzoate and the lower alkyl ester of the aromatic acid is ethyl benzoate.

29. The method of claim 28, wherein a ratio of the aromatic alcohol to the ester of the aromatic acid is in the range of about 1% to about 99% by weight.

30. The method of claim 29, wherein the ratio of the aromatic alcohol to the ester of the aromatic acid is in the range of about 20% to about 80% by weight.

31. The method of claim 27, wherein the thixotropic agent is ethanol.

32. The method of claim 25, wherein the thixotropic agent is ethanol.

33. The method of claim 32, wherein an amount of the ethanol is greater than or equal to 0.01 weight percent and less than or equal to 15 weight percent of the combined weight of the solvent and the thixotropic agent.

34. The method of claim 33, wherein the amount of the ethanol is greater than or equal to 0.1 weight percent and less than or equal to 5 weight percent of the combined weight of the solvent and the thixotropic agent.

35. The method of claim 34, wherein the amount of ethanol is greater than or equal to 0.5 weight percent and less than or equal to 5 weight percent of the combined weight of the solvent and the thixotropic agent.

36. The method of claim 25, wherein the beneficial agent is selected from a drug, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents, antiproliferative agents, antimitotic agents, angiogenic agents, anticoagulants, fibrinolytic agents, growth factors, antibodies, and ocular drugs.

37. The method of claim 36, wherein the beneficial agent is a growth factor.

38. The method of claim 36, wherein the beneficial agent is present in an amount of from 0.1 to 50% by weight of the combined amounts of the polymer, the solvent and the beneficial agent.

39. The method of claim 36, wherein the beneficial agent is in a form of particles dispersed or dissolved in the gel.

40. The method of claim 39 wherein the beneficial agent is in the form of the particles, wherein the particles further comprise a component selected from the group consisting of a stabilizing agent, bulking agent, chelating agent, and buffering agent.

41. The method of claim 36, wherein the beneficial agent is in the form of the particles having an average particle size of from 0.1 to 250 microns.

42. The method of claim 25, wherein the beneficial agent is a growth hormone.

43. A method of administering a beneficial agent to a subject to provide sustained release of the beneficial agent to the subject, the method comprising:
  (1) administering an injectable depot composition to the subject at a site within the subject, the composition comprising:
    (a) approximately 5 wt. % to approximately 90 wt. % of a poly(lactide-co-glycolide) (PLGA) copolymer having an average molecular weight in the range of approximately 1,000 to approximately 120,000;
    (b) approximately 5 wt. % to approximately 90 wt. % of a solvent selected from the group consisting of an aromatic alcohol, an ester of an aromatic acid, and mixtures thereof, said solvent having a miscibility in water of less than or equal to 7% at 25° C., and present in an amount effective to plasticize the polymer and form a gel therewith,
    (c) a thixotropic amount of a thixotropic agent mixed with the polymer effective to form a thixotropic composition, wherein the thixotropic agent is ethanol and an amount of ethanol is greater than or equal to 0.01 weight percent and less than or equal to 15 weight percent of the combined weight of the solvent and the thixotropic agent; and
    (d) a beneficial agent; and
  (2) forming an implant at the site wherein the implant provides sustained release of the beneficial agent at the site;
  wherein the injectable depot composition does not comprise an emulsion.

44. The method of claim 43, wherein the aromatic alcohol is benzyl alcohol and the ester of the aromatic acid is benzyl benzoate.

* * * * *